(12) United States Patent
Liu et al.

(10) Patent No.: US 10,535,165 B2
(45) Date of Patent: Jan. 14, 2020

(54) RECONSTRUCTING IMAGE

(71) Applicant: Shenyang Neusoft Medical Systems Co., Ltd., Shenyang (CN)

(72) Inventors: Shaolian Liu, Shenyang (CN); Zhipeng Sun, Shenyang (CN); Yunda Li, Shenyang (CN)

(73) Assignee: Shenyang Neusoft Medical Systems Co., Ltd., Shenyang, Liaoning (CN)

( * ) Notice: Subject to any disclaimer, the term of this patent is extended or adjusted under 35 U.S.C. 154(b) by 240 days.

(21) Appl. No.: 15/604,859

(22) Filed: May 25, 2017

(65) Prior Publication Data
US 2017/0345189 A1    Nov. 30, 2017

(30) Foreign Application Priority Data

May 25, 2016  (CN) .......................... 2016 1 0355835
Apr. 17, 2017  (CN) .......................... 2017 1 0249045

(51) Int. Cl.
| G06K 9/00 | (2006.01) |
| G06T 11/00 | (2006.01) |
| A61B 6/04 | (2006.01) |
| A61B 6/03 | (2006.01) |
| A61B 6/00 | (2006.01) |

(52) U.S. Cl.
CPC .......... *G06T 11/003* (2013.01); *A61B 6/037* (2013.01); *A61B 6/0457* (2013.01); *A61B 6/4208* (2013.01); *A61B 6/4241* (2013.01); *A61B 6/5205* (2013.01); *G06T 11/008* (2013.01)

(58) Field of Classification Search
None
See application file for complete search history.

(56) References Cited

U.S. PATENT DOCUMENTS 6,373,059 B1 *  4/2002  Stearns .................. G01T 1/2985
                                                                250/363.03
2011/0127436 A1 *  6/2011  Hashizume ........... G01T 1/1611
                                                                250/363.04

OTHER PUBLICATIONS

Brasse, David, et al. "Correction methods for random coincidences in fully 3D whole-body PET: impact on data and image quality." Journal of nuclear medicine 46.5 (2005): 859-867. (Year: 2005).*

* cited by examiner

*Primary Examiner* — Sean M Conner
(74) *Attorney, Agent, or Firm* — Fish & Richardson P.C.

(57) ABSTRACT

Methods, devices, and apparatus, including computer programs encoded on a computer storage medium for reconstructing image are provided. In one aspect, a method of reconstructing image includes obtaining scanning data for a subject in a continuous incremental scanning of medical equipment including real crystals for detection, associating each of the real crystals with one or more virtual crystals in a virtual scanning system, determining delay random coincidence data of two virtual crystals connected by a response line in the virtual scanning system, obtaining random coincidence data by denoising the delay random coincidence data based on crystal receiving efficiency for each of the real crystals, and reconstructing an image with the scanning data by taking the random coincidence data into account.

16 Claims, 10 Drawing Sheets

RECONSTRUCTING IMAGE

CROSS REFERENCE TO RELATED APPLICATIONS

The present disclosure claims priority to Chinese Patent Application No. 201610355835.8, which is filed on May 25, 2016 and Chinese Patent Application No. 201710249045.6, which is filed on Apr. 17, 2017, the entire content of which are incorporated herein by reference.

TECHNICAL FIELD

The present disclosure relates to reconstructing image in the field of medical technology.

BACKGROUND

The clinical examination imaging technology may include a plurality of techniques. One of these techniques is: a substance (generally essential substances of biological metabolism, e.g., glucose, protein and the like), which is marked with short-lived radioactive nuclides (e.g., 18F, 11C or the like), is injected into a subject, e.g., a patient. And then the subject may lie on a scanning bed to receive a scan in a detecting device. When scanning, the radioactive nuclides in the subject may release a positron e+ during a decay process. When the positron e+ meets a negatron e− in the subject, a positron annihilation event may occur. The positron annihilation event may generate two back-to-back γ-photons. The detecting device may receive the two γ-photons and perform an analysis based on receiving information (e.g., receiving time, receiving positions, or the like) of the two γ-photons. In an example, if the detecting device receives one or more γ-photons in a given time difference, it means that a coincidence event is detected. An internal image of the subject may be reconstructed based on information of the coincidence event. The image may reflect the metabolism activity of the subject, thereby achieving the purpose of diagnosing the subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, systems, and computer-readable mediums for reconstructing image, which can obtain random coincidence data from detected coincidence data to thereby improve quality of the reconstructed image.

One innovative aspect of the subject matter described in the present disclosure can be embodied in methods that include the actions of obtaining scanning data for a subject in a continuous incremental scanning mode of a real scanning system including real crystals for detection, the scanning data including information of single-photons received by each of the real crystals when the real crystal relatively moves to a scanning position on the subject in the continuous incremental scanning mode; constructing a virtual scanning system including a plurality of virtual crystals, each of the virtual crystals being associated with one or more real crystals each having a same relative position relationship with a respective scanning position on the subject in the real scanning system as the virtual crystal with the respective scanning position in the virtual scanning system; determining, based on the scanning data, delay random coincidence data of two virtual crystals connected by a response line in the virtual scanning system, the response line corresponding to a particular scanning position on the subject; denoising the delay random coincidence data based on a crystal receiving efficiency for each of a plurality of real crystals associated with the two virtual crystals and the particular scanning position; and reconstructing an image with the scanning data by using the denoised delay random coincidence data.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. The method can further include: obtaining a single-photon counting rate for each of the plurality of real crystals; and generating the crystal receiving efficiency for the real crystal according to the single-photon counting rate for the real crystal. In some examples, obtaining the single-photon counting rate for the real crystal includes: determining a number of single-photons received by the real crystal according to the scanning data; and generating the single-photon counting rate for the real crystal according to the number of single-photons and a time for receiving the single-photons. In some examples, obtaining the single-photon counting rate for the real crystal includes: determining a plurality of single-photon counting components corresponding to the particular scanning position of the subject, wherein each of the single-photon counting components includes a number of single-photons received by a corresponding real crystal of the plurality of real crystals when the corresponding real crystal moves to the particular scanning position; determining, according to the plurality of single-photon counting components, a number of single-photons received by one of the two virtual crystals associated with the real crystal; generating a single-photon counting rate for the one of the two virtual crystals according to the number of single-photons received by the one of the two virtual crystals and scanning time corresponding to the particular scanning position; and generating the single-photon counting rate for the real crystal according to the single-photon counting rate for the one of the two virtual crystals and a proportional relationship between real crystals associated with the one of the two virtual crystals.

In some implementations, generating the crystal receiving efficiency for the real crystal according to the single-photon counting rate for the real crystal includes generating the crystal receiving efficiency for the real crystal according to the single-photon counting rate for the real crystal and a relationship between single-photon counting rate and crystal receiving efficiency for the real crystal under different doses. The method can further include: determining, under a particular dose, a single-photon counting rate for the real crystal and a mean value of single-photon counting rates for a number of real crystals including the real crystal; determining a crystal receiving efficiency of the real crystal under the particular dose based on the determined single-photon counting rate for the real crystal and the mean value of single-photon counting rates of the number of real crystals; and determining the relationship based on a ratio between the determined crystal receiving efficiency of the real crystal and the single-photon counting rate under the particular dose. In some implementations, generating the crystal receiving efficiency for the real crystal according to the single-photon counting rate for the real crystal includes: under a same dose, determining a ratio between the single-photon counting rate for the real crystal and a mean value of the single-photon counting rates for a number of real crystals including the real crystal; and taking the determined ratio as the crystal receiving efficiency for the real crystal.

In some implementations, denoising the delay random coincidence data includes: determining a respective crystal receiving efficiency of each of the plurality of real crystals; determining a crystal pair receiving efficiency for the two virtual crystals according to the crystal receiving efficiencies of the plurality of real crystals; and denoising the delay random coincidence data according to the determined crystal pair receiving efficiency. In some examples, a first virtual crystal of the two virtual crystals is associated with a plurality of first real crystals, a second virtual crystal of the two virtual crystals is associated with a plurality of second real crystals, and each of the first real crystals corresponds to a respective one of the second real crystals for the particular scanning position. Determining the crystal pair receiving efficiency for the two virtual crystals can include: multiplying a first crystal receiving efficiency for each of the first real crystals with a second crystal receiving efficiency for a second real crystal corresponding to the first real crystal to get a multiplied result; and determining the crystal pair receiving efficiency for the two virtual crystals by averaging the multiplied results.

The method can further include: determining, based on the scanning data, second delay random coincidence data of another two virtual crystals connected by a second response line in the virtual scanning system, the second response line corresponding to a second scanning position on the subject; denoising the second delay random coincidence data based on a crystal receiving efficiency for each of a second plurality of real crystals associated with the another two virtual crystals and the second particular scanning position; and reconstructing the image with the scanning data using the denoised second delay random coincidence data.

The method can further include obtaining random coincidence data by, with an assumption that the two virtual crystals are virtual crystal i and virtual crystal j on the response line, the virtual crystal i belonging to a set A comprising m number of first virtual crystals and the virtual crystal j belonging to a set B comprising m number of second virtual crystals, denoising: delay random coincidence data for the virtual crystal i and a virtual crystal l among the set B according to a crystal pair receiving efficiency for the virtual crystal i and the virtual crystal l; delay random coincidence data for the virtual crystal j and a virtual crystal k among the set A according to a crystal pair receiving efficiency for the virtual crystal j and the virtual crystal k; and delay random coincidence data for the virtual crystal l and the virtual crystal k according to a crystal pair receiving efficiency for the virtual crystal l and the virtual crystal k, i, j, k and l are non-negative integers; and reconstructing the image with the scanning data by using the obtained random coincidence data.

Another innovative aspect of the subject matter described in the present disclosure can be embodied in a device for reconstructing image applied to medical equipment including real crystals. The device includes a processor configured to execute machine executable instructions corresponding to control logic for reconstructing image stored on a machine readable storage medium such that when the machine executable instructions are executed, the processor is caused to: obtain scanning data for a subject in a continuous incremental scanning mode of the medical equipment; associate each of the real crystals with one or more virtual crystals in a virtual scanning system; determine, according to the scanning data, delay random coincidence data of two virtual crystals connected by a response line in the virtual scanning system; obtain random coincidence data by denoising the delay random coincidence data based on a crystal receiving efficiency for each of a plurality of real crystals associated with the two virtual crystals; and reconstruct an image with the scanning data by taking the random coincidence data into account.

The foregoing and other embodiments can each optionally include one or more of the following features, alone or in combination. The machine executable instructions can further cause the processor to: obtain a single-photon counting rate for each of the real crystals; and determine the crystal receiving efficiency for the real crystal according to the single-photon counting rate for the real crystal. In some examples, the machine executable instructions cause the processor to obtain the single-photon counting rate for each of the real crystals by determining a number of single-photons received by the real crystal; and generating the single-photon counting rate for the real crystal according to the number of single-photons and a time for receiving the single-photons. In some examples, the machine executable instructions cause the processor to obtain the single-photon counting rate for each of the real crystals by obtaining a plurality of single-photon counting components corresponding to a scanning position of the subject; determining a number of single-photons received by a virtual crystal associated with the scanning position according to the plurality of single-photon counting components; determining a single-photon counting rate for the virtual crystal according to the number of single-photons received by the virtual crystal and scanning time corresponding to the scanning position; and generating the single-photon counting rate for the real crystal associated with the virtual crystal according to the single-photon counting rate for the virtual crystal, where each of the single-photon counting components is a number of single-photons received by a real crystal when the real crystal moves to the scanning position and the real crystal and the virtual crystal have the same relative position relationship with the scanning position.

In some implementations, the machine executable instructions cause the processor to determine the crystal receiving efficiency for the real crystal according to the single-photon counting rate for the real crystal by determining the crystal receiving efficiency for the real crystal according to the single-photon counting rate for the real crystal and a function indicating a relationship between single-photon counting rate and crystal receiving efficiency for the real crystal under different doses. In some implementations, the machine executable instructions cause the processor to determine the crystal receiving efficiency for the real crystal according to the single-photon counting rate for the real crystal by under a same dose, determining a ratio between the single-photon counting rate for the real crystal and a mean value of the single-photon counting rates for all the real crystals; and taking the ratio as the crystal receiving efficiency for the real crystal.

The machine executable instructions can cause the processor to obtain the random coincidence data by denoising the delay random coincidence data according to the crystal receiving efficiency for the real crystal by determining two virtual crystals on the response line and real crystals associated with the two virtual crystals on the response line; determining a crystal receiving efficiency for each of the determined real crystals; generating a crystal pair receiving efficiency for the two virtual crystals according to the crystal receiving efficiency for each of the determined real crystals; and obtaining the random coincidence data by denoising the delay random coincidence data according to the crystal pair receiving efficiency.

The machine executable instructions can cause the processor to generate the crystal pair receiving efficiency for the two virtual crystals by with an assumption that the two virtual crystal are virtual crystal i and virtual crystal j on the response line, determining m number of first real crystals associated with the virtual crystal i on the response line and m number of second real crystals associated with the virtual crystal j on the response line, i, j and m being non-negative integers, and generating the crystal pair receiving efficiency for the virtual crystal i and the virtual crystal j according to crystal receiving efficiencies for the m number of first real crystals and crystal receiving efficiencies for the m number of second real crystals.

The machine executable instructions can also cause the processor to obtain the random coincidence data by denoising the delay random coincidence data according to the crystal pair receiving efficiency by with an assumption that the two virtual crystal are virtual crystal i and virtual crystal j on the response line, the virtual crystal i belonging to a set A comprising m number of first virtual crystals and the virtual crystal j belonging to a set B comprising m number of second virtual crystals, obtaining the random coincidence data by denoising: delay random coincidence data for the virtual crystal i and a virtual crystal l among the set B according to a crystal pair receiving efficiency for the virtual crystal i and the virtual crystal l, delay random coincidence data for the virtual crystal j and a virtual crystal k among the set A according to a crystal pair receiving efficiency for the virtual crystal j and the virtual crystal k, and delay random coincidence data for the virtual crystal l and the virtual crystal k according to a crystal pair receiving efficiency for the virtual crystal l and the virtual crystal k, where i, j, k and l are non-negative integers.

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
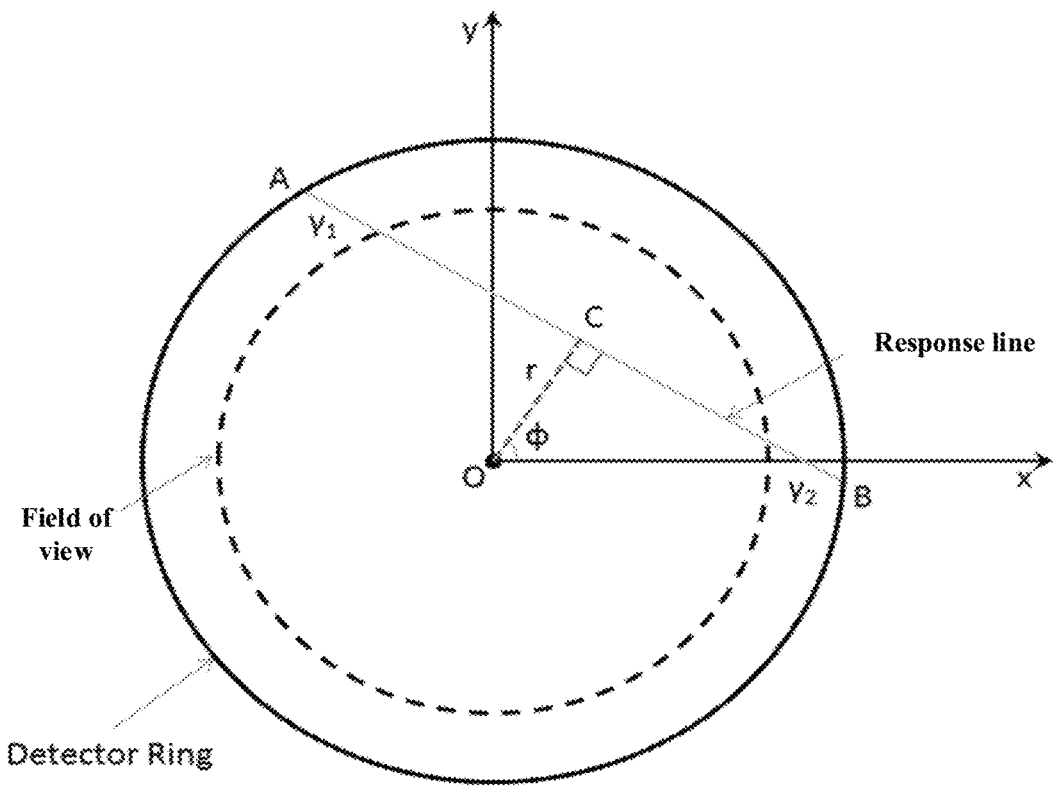
FIG. 1 is a schematic diagram of a collection scanning data scenario according to one or more examples of the present disclosure.

The present disclosure provides a method of reconstructing image. When a subject is scanned in a continuous incremental scanning mode, the method may be used to reconstruct an image. The method of reconstructing image may be applied to medical equipment. The medical equipment may include a Computed Tomography (CT) system, a Positron Emission Computed Tomography (PET) system, a Digital Radiography (DR) system, a Magnetic Resonance Imaging (MRI) system, or the like. In the following, the method of reconstructing image is described by taking the PET system as an example. It may be understood that the method of reconstructing image may also be applied to other systems.

Scan modes of the PET system may include a step scanning mode and a continuous incremental scanning mode. The step scanning mode may mean that: with the subject lying on the scanning bed, when the scanning bed moves to a position, a scanning for the subject may be carried out for a period of time, and when the scanning is completed and the scanning bed moves to a next position, the subject may be scanned for another period of time. The continuous incremental scanning mode may mean that: with the subject lying on the scanning bed, the scanning bed moves at a constant speed, thereby performing a continuous scanning for the subject.

If more than two γ-photons are detected by a detecting device in a given time difference, it is referred to as a multiple-coincidence event. During reconstructing image, the multiple-coincidence event may be discarded. If two γ-photons are detected by the detecting device in a given time difference, it is referred to as a two-coincidence event. Data corresponding to the two-coincidence event may be used to reconstruct image. For simplicity, a coincidence event in the present disclosure refers to a two-coincidence event.

If two detected γ-photons are from the same positron annihilation event and the two γ-photons both have no angular deflection, it may be referred to as a true coincidence event. If the two detected γ-photons are from the same positron annihilation event, and at least one γ-photon has angular deflection, it may be referred to as a scatter coincidence event. If the two detected γ-photons are from different positron annihilation events, it may be referred to as a random coincidence event. Data obtained by coincidence events may be referred to as coincidence data. For example, data obtained by a random coincidence event may be referred to as random coincidence data.

As the detected coincidence events may include a true coincidence event, a scatter coincidence event and a random coincidence event, coincidence data corresponding to the true coincidence event can be obtained by distinguishing the scatter coincidence event and the random coincidence event from the detected coincidence events, which may enable to reconstruct an image with relative high quality. In some cases, random coincidence data can also serve as a factor for reconstructing image. For example, when reconstructing an image according to an Ordinary-Poisson OSEM (ordered subset expectation maximization) method, prompt coincidence data from scanning data may follow Poisson distribution, for example, p~P(λ) where p may represent the prompt coincidence data and λ may be an expectation value of p. An iterative formula according to the Ordinary-Poisson OSEM method can be as follows:

$$x_j^{k+1} = \frac{x_j^k}{\sum_i n_i a_i g_{ij}} \sum_i \frac{n_i a_i g_{ij} p_i}{n_i a_i \left(\sum_j g_{ij} x_j^k\right) + n_i s_i + r_i},$$

where, $x_j^k$ may represent a reconstructed image pixel, j may represent a pixel number, k may represent iteration number, i may represent a coincidence data number, $n_i$ may represent a normalization factor, $a_i$ may represent an attenuation factor, $g_{ij}$ may represent a geometric projection factor from j to i, $n_i s_j$ may represent scatter coincidence data and $r_i$ may represent random coincidence data.

Implementations of the present disclosure provide a method of obtaining random coincidence data for reconstructing image. Particularly, delay random coincidence data can be first obtained during scanning by a delay circuit, and then, due to high noise of the delay random coincidence data, the delay random coincidence data can be denoised to obtain denoised delay random coincidence data, which can be used as random coincidence data for reconstructing image. In the delay circuit, assuming there is a pair of crystals on a response line, a time for a coincidence event that a crystal of the pair of crystals receives a photon is delayed for a given time and a time for the coincidence time that another crystal of the pair of crystals receives another photon remains unchanged.

Coincidence data can be obtained from scanning data. FIG. 1 is a schematic diagram of a collection scanning data scenario according to one or more examples of the present disclosure. As shown in FIG. 1, if a real crystal A and a real crystal B in a PET system receive, in a coincidence time window, photons $\gamma_1$ and $\gamma_2$ generated by a positron annihilation event, respectively (the receiving case may be known from scanning data), it may be referred to as a coincidence event occurring. The scanning data may include the receiving information of the real crystal A and the real crystal B. The coincidence data can be incremented by 1 every time when a coincidence event occurs.

Coincidence data of the real crystal A and the real crystal B can be obtained. In some implementations, a distance r from a center O of a field of view to a line connecting the real crystal A and the real crystal B serves as a radial coordinate, and an included angle φ between a line OC through the center O and perpendicular to the line connecting the real crystal A and the real crystal B and the x-axis serves as an angular coordinate, and (r, φ) may uniquely represent positions corresponding to a pair of real crystals. A sinogram is a storage format for coincidence data, which encodes a coincidence event according to a corresponding coincidence radial position (r, φ) and stores (r, φ) in a matrix. An image formed by the matrix is the sinogram. An accumulated sum of the number of coincidence events occurring at (r, φ) may be regarded as a value at (r, φ) in the matrix, and the value at (r, φ) in the matrix may be the coincidence data for the real crystal A and the real crystal B.

In practical application, coincidence data form scanning data may include prompt coincidence data and delay random coincidence data. The prompt coincidence data may be a sum of true coincidence data, scatter coincidence data and random coincidence data. The prompt coincidence data may be used to reconstruct image according to the above description. The delay random coincidence data may be used to obtain the random coincidence data, e.g., by denoising the delay random coincidence data.

Figure 2A:
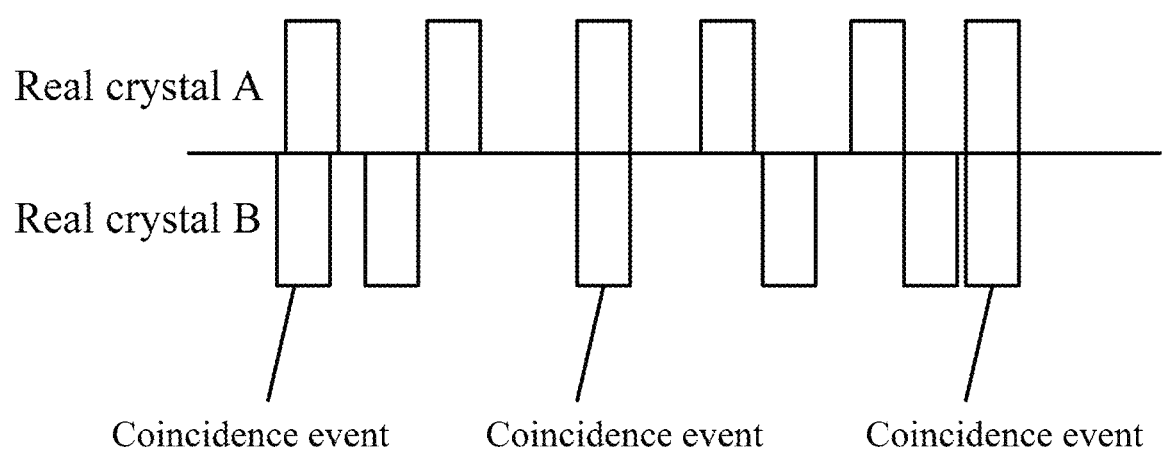
FIG. 2a is a schematic diagram of a prompt sinogram according to one or more examples of the present disclosure.

Regarding prompt coincidence data, based on the scanning data (where photons $\gamma_1$ and $\gamma_2$ generated by positron annihilation events are received) of the real crystal A and the real crystal B, events that the real crystal A and the real crystal B receive photons $\gamma_1$ and $\gamma_2$ may be chronologically arranged into two rows. FIG. 2a is a schematic diagram of a prompt sinogram according to one or more examples of the present disclosure, where the upper row shows events that the real crystal A receives photon $\gamma_1$, and the lower row shows events that the real crystal B receives photon $\gamma_2$. If a time difference between a time for the real crystal A receiving photon $\gamma_1$ and a time for the real crystal B receiving photon $\gamma_2$ is within the coincidence time window, it may be considered that a coincidence event occurs, and prompt coincidence data may be incremented by 1. As shown in FIG. 2a, it may be considered that three coincidence events occur altogether, and therefore, the prompt coincidence data is 3.

Figure 2B:
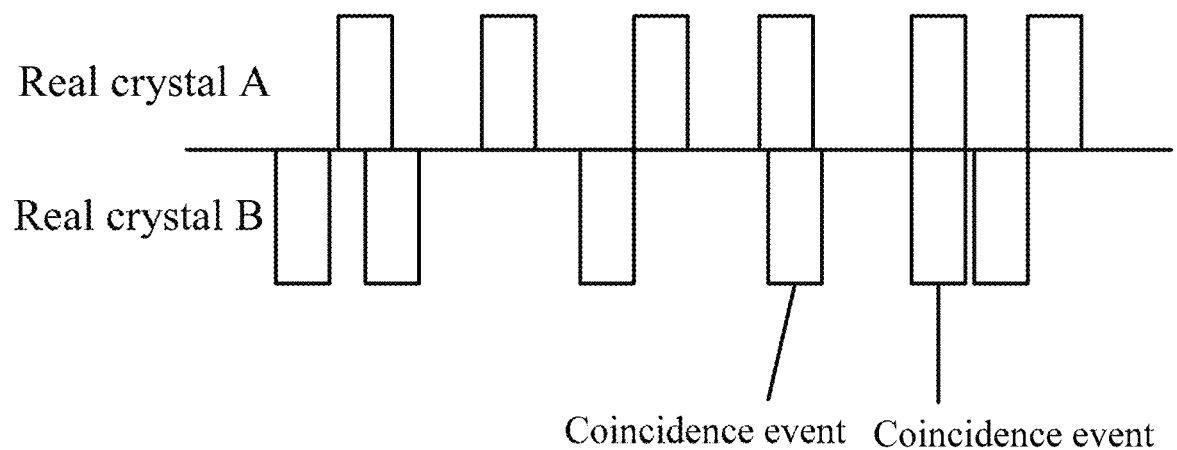
FIG. 2b is a schematic diagram of a delay sinogram according to one or more examples of the present disclosure.

Regarding delay random coincidence data, it may be obtained by using a delay coincidence window. For example, based on the scenario of FIG. 2a, after the events that the real crystal A and the real crystal B receive photons $\gamma_1$ and $\gamma_2$ are chronologically arranged into two rows, respectively, any one of the two rows may be delayed for a given time. FIG. 2b shows a schematic diagram of an example delay sinogram. The delay sinogram illustrates that a time for an event that the real crystal A receives a photon $\gamma_1$ is delayed for a given time and a time for the event that the real crystal B receives a photon $\gamma_2$ remains unchanged. Based on this, if a time difference between the delayed time for the event that the real crystal A receives a photon $\gamma_1$ and the time for the event that the real crystal B receives a photon $\gamma_2$ is within the coincidence time window, it may be considered that a coincidence event occurs, and delay random coincidence data may be incremented by 1. As shown in FIG. 2b, it may be considered that two coincidence events occur altogether, and therefore, the delay random coincidence data is 2.

Due to a high noise level of the delay random coincidence data obtained by using the delay coincidence window, it may be required to perform a de-noise process on the delay random coincidence data. However, in the continuous incremental scanning mode, there is no effective method for denoising the delay random coincidence data at present. Implementations of the present disclosure provides a method of denoising the delay random coincidence data in the continuous incremental scanning mode to obtain denoised delay random coincidence data, so that the obtained denoised random coincidence data (random coincidence data) can be distinguished from prompt coincidence data to make data used in image reconstruction more accurate, thereby improving the quality of image reconstruction.

Figure 3:
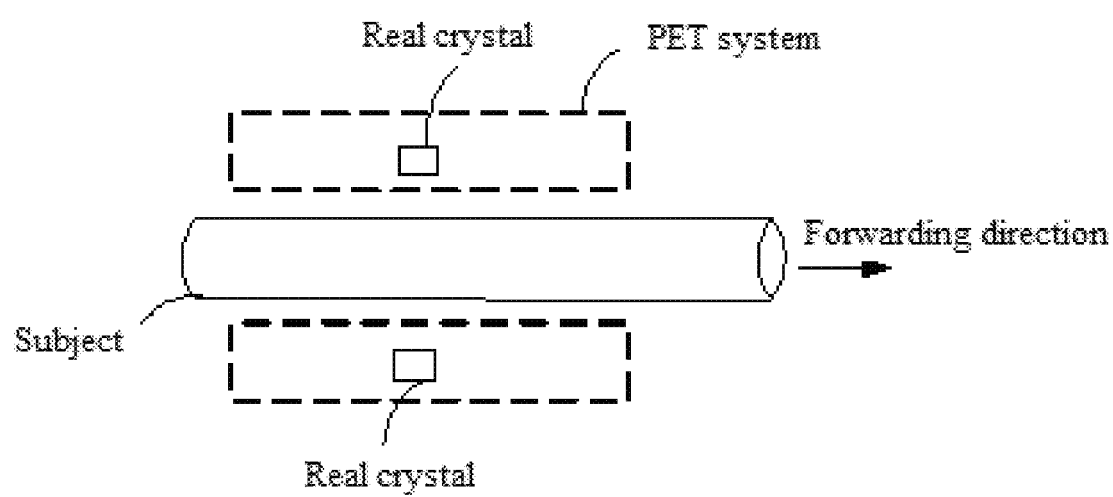
FIG. 3 is a schematic diagram of a Positron Emission Computed Tomography (PET) continuous incremental scanning scenario according to one or more examples of the present disclosure.
Figure 4:
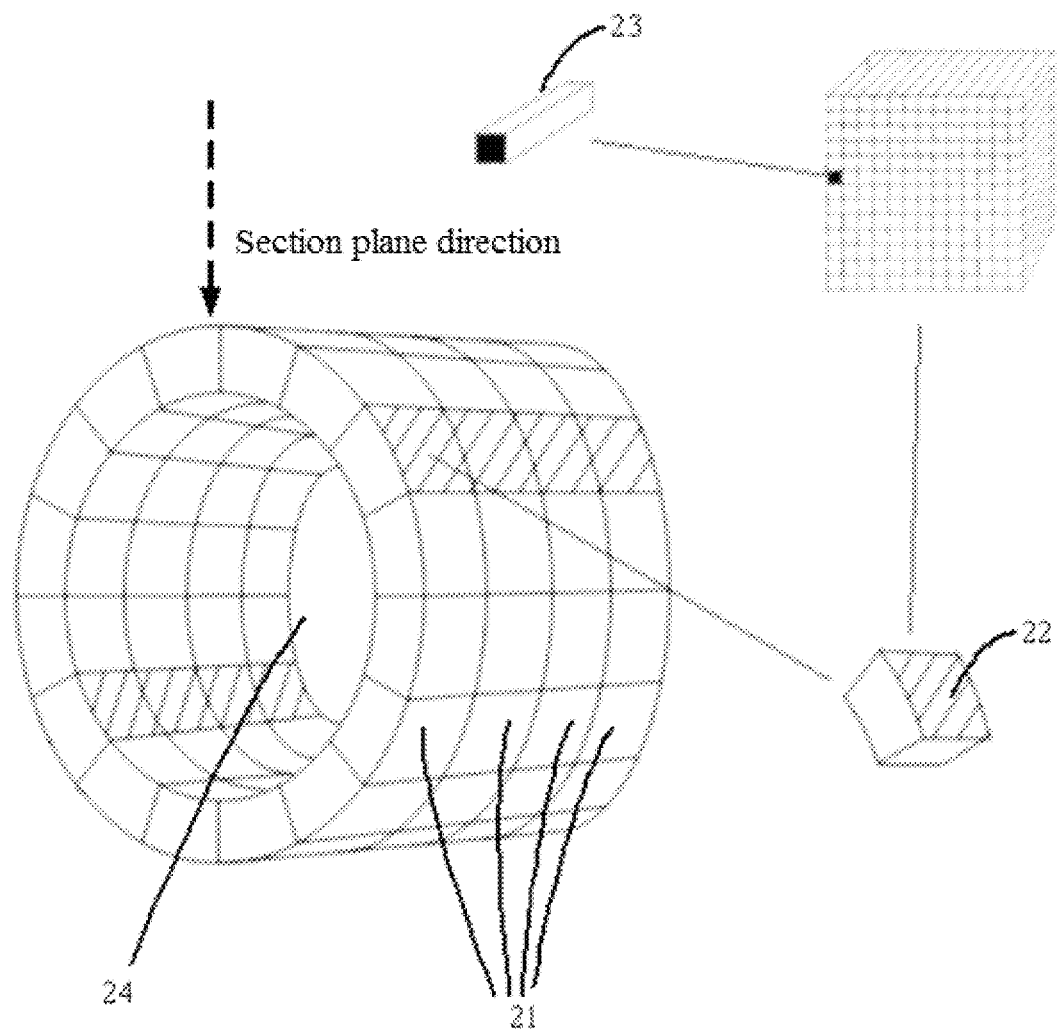
FIG. 4 is a perspective schematic diagram of a PET system according to one or more examples of the present disclosure.

FIG. 3 illustrates a schematic diagram of a subject in a continuous incremental scanning in a PET system. In FIG. 3, the arrow may indicate a forward direction of the scanning bed (for example, the subject lies on the scanning bed, and the scanning bed moves in the direction indicated by the arrow), and the scanning bed may move at a constant speed. The PET system shown in FIG. 3, actually a section plane of the PET system, may include a plurality of detector rings (as illustrated in FIG. 4). FIG. 4 is a perspective diagram of the PET system including four detector rings 21 therein. In practical application, there may be a greater number of detector rings. The detector ring may also be referred to as a block ring. Each detector ring may include a plurality of blocks 22, and each Block 22 may include a plurality of crystals 23. A plurality of detector rings may constitute an internal space 24 where a subject lies, and a single-photon (e.g., a γ-photon) generated by a positron annihilation event occurring in the internal space may be received by a crystal 23 in a detector ring. The PET system shown in FIG. 3 may be obtained by the section plane direction indicated by the dotted arrow in FIG. 4. As can be seen in FIG. 4, it may be understood that the PET system includes a plurality of crystal rings, each crystal ring is a ring-shaped crystal string in the circumferential direction of the detector rings 21, and the ring-shaped crystal string includes numerous single crystals, for example, 100 crystals.

Figure 5:
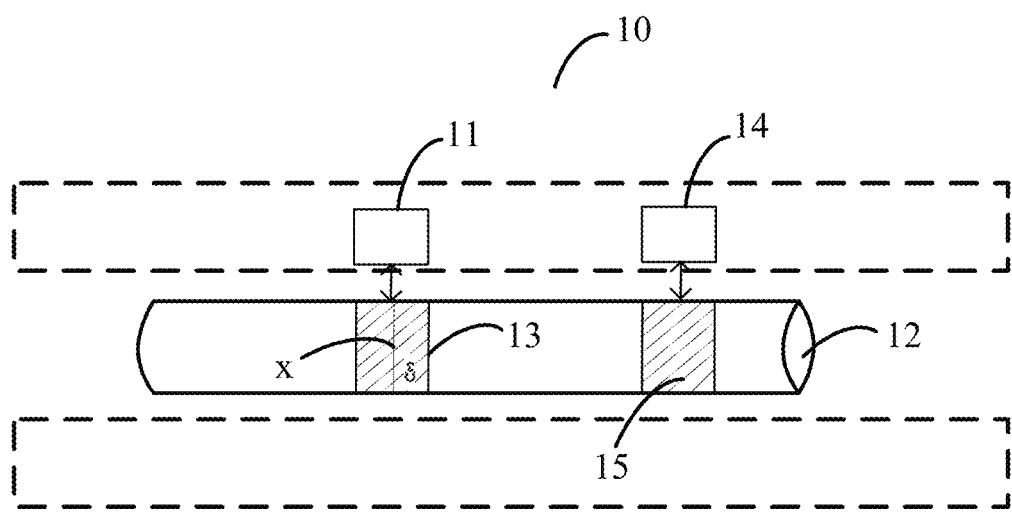
FIG. 5 is a schematic diagram of a virtual PET system according to one or more examples of the present disclosure.

A virtual PET system may be defined according to an example of the present disclosure. Actually, a virtual PET system may be formed in a way that a real crystal is associated with one or more virtual crystals, and a correspondence between a real crystal and a virtual crystal may be determined according to the information of the real crystal position and scanning position. FIG. 5 shows a schematic diagram of an example virtual PET system 10. The virtual PET system 10 may include a plurality of virtual crystals. For example, the size of the virtual crystal 11 may be consistent with that of a real crystal of the PET system. For convenience of distinguishing, crystals in the virtual PET system may be referred to as virtual crystals, and crystals in the real PET system may be referred to as real crystals.

Further, the virtual PET system 10 may also include a plurality of detector rings which are identical formally with those in the real PET system shown in FIG. 4. FIG. 5 is a section plane diagram of the virtual PET system. The virtual PET system differs from the real PET system in that the virtual PET system 10 is larger than the real PET system mainly because the number of the detector rings may increase. For example, the real PET system may include 20 detector rings, while the virtual PET system may include 40 detector rings, where the numbers are merely taken for example. The reason that the virtual PET system 10 is larger than the real PET system is: as can be seen in FIG. 3, the length of the actual PET system in the forward direction (which may be hereinafter referred to as Z-axis) is usually smaller than the length of the subject, and as can be seen in FIG. 5, the length of the virtual PET system in the direction of Z-axis is greater than the length of the subject. In this way, a continuous incremental scanning performed by the real PET system may be equivalent to that a subject may have a scan on different parts of the whole body by staying still in the virtual PET system 10.

Each virtual crystal in the virtual PET system 10 shown in FIG. 5 may be associated with a scanning position of the subject. For example, as shown in FIG. 5, the virtual crystal 11 is associated with the scanning position 13 of the subject. As the length of the virtual crystal 11 is consistent with that of a real crystal in the real PET system, a scanning position associated with a virtual crystal may also be regarded as a length of a real crystal. For example, assuming that the middle position x of the scanning position 13 is a point position on the subject, a range (x−δ, x+δ) may be regarded as the above-mentioned scanning position 13, and δ is a half of the size of a real crystal. The scanning position 15 may be associated with the virtual crystal 14. It can be seen that each virtual crystal may be associated with a scanning position of the subject 12.

Further, with regard to the above description that each virtual crystal is associated with a scanning position, it may be understood as follows: assuming that the subject 12 is scanned in the virtual PET system 10, the above-mentioned scanning position 13 of the subject 12 may correspond to the virtual crystal 11. It may be similar to that each of the real crystals corresponds to the scanning position in due order when the scanning bed is kept in a traditional step scanning mode.

Figure 6:
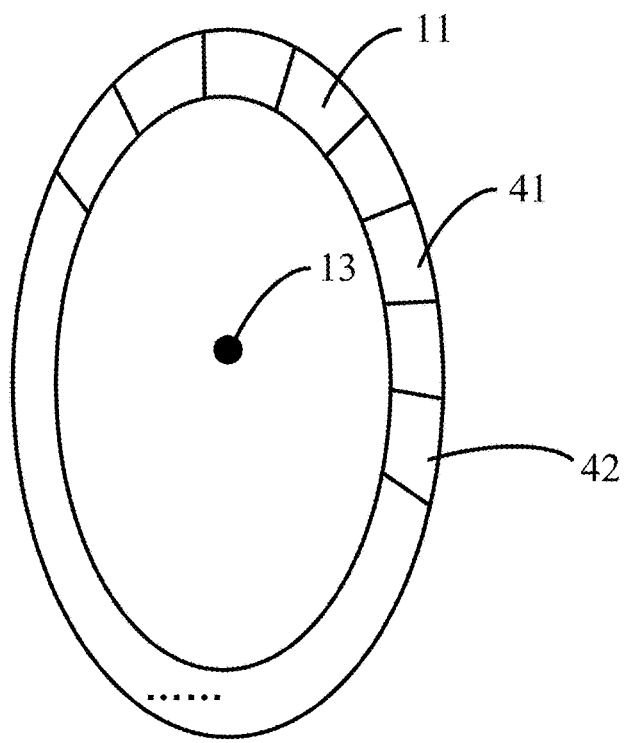
FIG. 6 is a schematic diagram of a crystal ring according to one or more examples of the present disclosure.

In addition, as mentioned above, FIG. 5 merely illustrates a section plane of the virtual PET system. Actually, the virtual PET system can be also a ring-shaped detecting device, which is similar to the stereoscopic system shown in FIG. 4. When the subject is placed in the internal space of the virtual PET system, a plurality of virtual crystals corresponds to a particular scanning position, and the plurality of virtual crystals is arranged to form a crystal ring. Referring to in FIG. 6, taking the scanning position 13 for example, a plurality of crystals such as the virtual crystal 11, the virtual crystal 41 and the virtual crystal 42 in a detector ring may all correspond to the scanning position 13. That is, a plurality of virtual crystals in a detector ring corresponds to a particular scanning position, and the virtual crystals are just different in angle with respect to the scanning position. It is conceivable that when the subject lies on the scanning bed and stays in the internal space 24 shown in FIG. 4, the subject actually stays inside a ring-shaped detecting device, and any scanning position of the subject may correspond to a plurality of virtual crystals in a detector ring.

As can be seen from the above descriptions, when the subject is scanned in the continuous incremental mode in the real PET system, the scanning bed moves constantly. But assuming that there is a PET system with stationary scanning bed, it is equivalent to the subject placed in virtual PET system 10 shown in FIG. 5 and scanned stationary. Each virtual crystal in the virtual PET system 10 may be associated with a scanning position of the subject.

In an example of the present disclosure, if delay random coincidence data on a response line is denoised by using the virtual PET system 10 shown in FIG. 5, the following process may be executed: obtaining a single-photon counting rate for a virtual crystal on the response line; obtaining crystal receiving efficiency for each of the real crystals associated with the virtual crystal on the response line; and denoising the delay random coincidence data according to the crystal receiving efficiency.

An example of obtaining a single-photon counting rate for a virtual crystal is provided below, and detailed description may not be limited to the following illustrated method. To obtain a single-photon counting rate for a virtual crystal, a number of single-photons received by the virtual crystal may be obtained first. Next, the single-photon counting rate for the virtual crystal may be obtained according to the obtained number of single-photons received by the virtual crystal and scanning time of a scanning position associated with the virtual crystal. For example, the single-photon counting rate for the virtual crystal may be obtained by dividing the number of single-photons of the virtual crystal by the scanning time.

In an example, when the subject is scanned, a number of single-photons received by each of the virtual crystals in the virtual PET system may be obtained. The single-photon count of a virtual crystal may be a number of single-photons (e.g., γ-photons generated in the positron annihilation events) received by the virtual crystal in the whole process of scanning. The number of single photons received by the virtual crystal may be referred to as the single-photon count of the virtual crystal.

Figure 7:
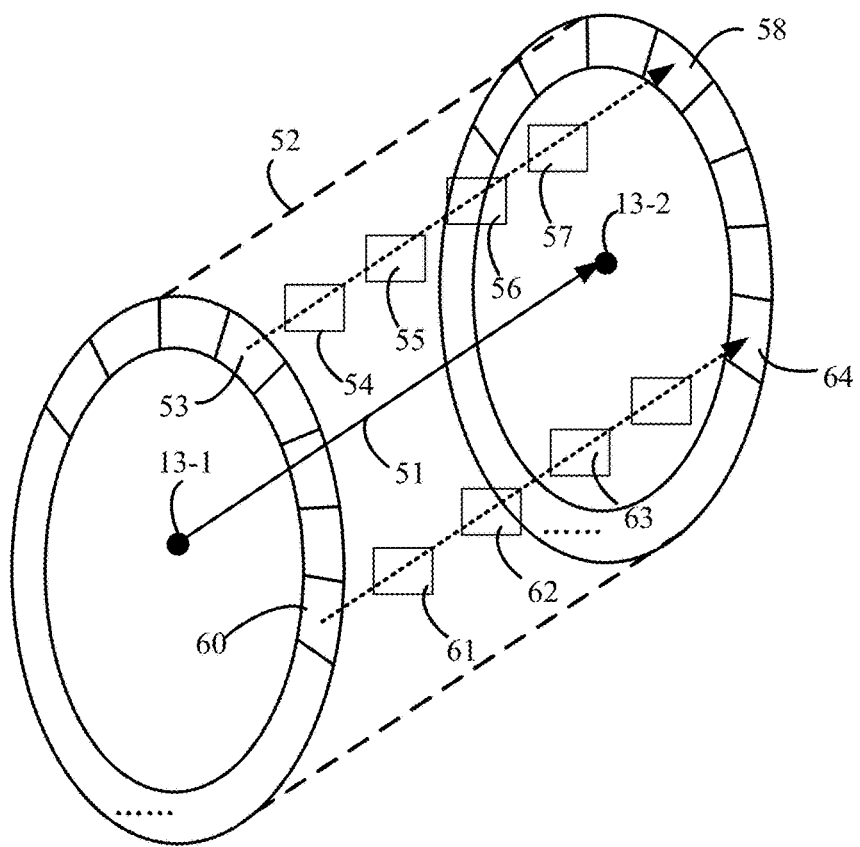
FIG. 7 is a schematic diagram of correspondence between a virtual crystal and a real crystal string according to one or more examples of the present disclosure.

The single-photon count of each of the virtual crystals is a sum of single-photon counts of a plurality of real crystals in the real PET system. Referring to FIG. 5 and FIG. 7, single-photon counts received by real crystals may be counted into a single-photon count of a virtual crystal associated with these real crystals.

As shown in FIG. 5, taking a scanning position such as the scanning position 13 on the subject 12 as an example, the scanning position 13 is associated with the virtual crystal 11. In the continuous incremental scanning mode, the subject may move along with the scanning bed and the scanning position 13 on the subject may also move together. FIG. 7 illustrates two endpoints 13-1, 13-2 of the scanning position 13 during scanning. The scanning position 13 begins to be scanned from the position of the starting point 13-1, moves along with the subject in the direction indicated by the arrow 51 (the forward direction of the scanning bed), and continues to be scanned until the scanning position 13 moves to the position of the finishing point 13-2 (for example, the scanning position 13 moves out of the virtual PET system 10). FIG. 7 also illustrates two crystal rings corresponding to the two endpoint positions 13-1,13-2, where the dotted line 52 may represent that there are still many crystal rings between the two crystal rings. It is conceivable that the system as shown in FIG. 7 is a stereoscopic real PET system and FIG. 7 only illustrates two crystal rings at two ends of the PET system.

Still referring to FIG. 7, a real crystal 53, a real crystal 54, and a real crystal 55 to a real crystal 58 (FIG. 7 illustrates only a part of real crystals, and the actual number of real crystals may be greater) may form a "crystal string", and the direction of the crystal string may be parallel to the forward direction indicated by the arrow 51. During the scanning process of the scanning position 13 moving from the position of the starting point 13-1 to the position of the finishing point 13-2, each of the real crystals in the above mentioned crystal string may move to the scanning position 13 at some timing. For example, when the scanning position 13 is located in the crystal ring at the leftmost end as shown in FIG. 7, the real crystal 53 is located in an axial position corresponding to the scanning position 13; when the scanning position 13 is located at the axial rightmost position in the crystal ring as shown in FIG. 7, the real crystal 58 is located in an axial position corresponding to the scanning position 13, and each of the real crystals between the real crystal 53 and the real crystal 58, such as the real crystal 54, the real crystal 55 and the like, may be located in an axial position corresponding to the scanning position 13.

Figure 8:
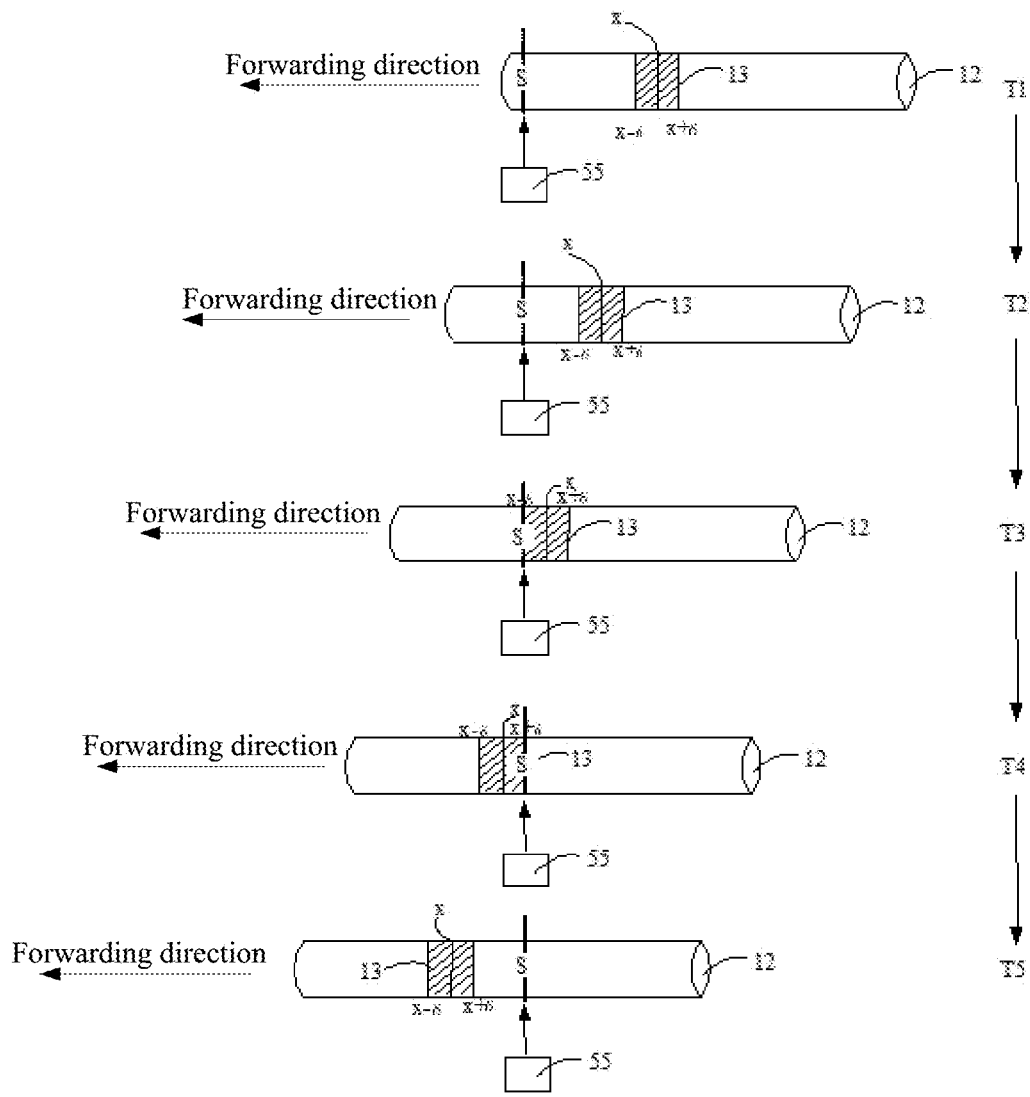
FIG. 8 is a schematic diagram of a scanning process according to one or more examples of the present disclosure.

FIG. 8 illustrates a schematic diagram of a motion process of the scanning position 13. As shown in FIG. 8, the real crystal 55 in the real PET system may be taken for example. FIG. 8 illustrates five moments T1, T2, T3, T4 and T5 in a continuous incremental scanning process. In a sequence of from the moment T1 to the moment T5, the subject 12 may move in the forward direction indicated by the arrow and may move forward at a given constant speed. Where, the position of the real crystal 55 is fixed, and a scanning position on the subject 12 corresponding to the center line S of the real crystal 55 also keeps moving as the subject 12 moves in the forward direction. At the moment T3, the left side "x−δ" of the scanning position 13 (x is the center line of the scanning position 13 and δ is a half of the length of a real crystal) reaches the center line S of the real crystal 55. At the moment T4, the right side "x+δ" of the scanning position 13 reaches the center line S of the real crystal 55. It may be regarded that the scanning position 13 corresponds to the real crystal 55 in the time period from T3 to T4.

According to the above-mentioned principle, during the continuous incremental process of the subject 12, for the crystal string from the real crystal 53 to the real crystal 58 shown in FIG. 7, each of the real crystals may relatively move to the scanning position 13 at some timing similar to that indicated by FIG. 8 and the number of single-photons received by the real crystal at the time period may be a part of the number of single-photons received by the virtual crystal 11 associated with the scanning position 13. When each of the real crystals including the real crystal 53 to the real crystal 58 relatively moves to the scanning position 13, the number of single-photons received by each of the real crystals in the crystal string from the real crystal 53 to the real crystal 58 may be accumulated, so as to obtain the single-photon count of the virtual crystal 11 associated with the scanning position 13 shown in FIG. 6. The correspondence between the virtual crystal 11 and the above-mentioned crystal string may be seen in FIG. 6 and FIG. 7. If assuming that the scanning position 13 is in the center of a detector ring, the position of the virtual crystal 11 may be identical with that of each of the real crystals in the above-mentioned crystal string in this detector ring. The real crystals 53-58 and the virtual crystal 11 have the same relative position relationship with the scanning position 13 in a case of corresponding to the scanning position 13. For example, if the detector ring is seen at 360 degrees, the real crystals 53-58 and the virtual crystal 11 may have the same angular position in the detector ring.

Similarly, in FIG. 7, another crystal string includes a real crystal 60, a real crystal 61, and real crystals 62 to 64. The number of single photons received by these real crystals in a case of corresponding to the scanning position 13 may be all accumulated to the virtual crystal 42 shown in FIG. 6. The single photon counts of other virtual crystals may be obtained according the above principle. For example, a single photon count for each of the virtual crystals may be obtained by accumulating the number of single-photons received by each of the real crystals in a crystal string that has the same angular position as the virtual crystal. If the number of single-photons received by a real crystal in a case of corresponding to a scanning position is referred to as a single-photon counting component, for a plurality of real crystals in a crystal string in the real PET system, a plurality of single-photon counting components corresponding to the scanning position may be accumulated so as to obtain the single-photon count of the virtual crystal associated with the scanning position.

In the scanning process, the single-photon count of each of the virtual crystals in the virtual PET system may be obtained by using the above-described method. For a virtual crystal, a scanning position of the subject associated with the virtual crystal and a crystal string in the real PET system associated with the virtual crystal may be determined first, and then the single-photon count of the virtual crystal may be obtained by accumulating the number of single-photons received by each of the real crystals when each of the real crystal in the above-mentioned crystal string moves to the scanning position in the whole scanning process.

In an example, to achieve the above-mentioned accumulation of the number of single-photons received by each of the real crystals, processing may be carried out as follows. After a real crystal receives a γ-photon, the receiving information of the γ-photon may be transmitted to a backend data processing system. The receiving information may include a receiving time of the γ-photon. The data processing system may determine a scanning position of the subject that corresponds to the γ-photon according to incremental motion information of the subject and the receiving time, and add up the number of single-photons received by the real crystal to the single-photon count of a virtual crystal associated with the above-mentioned scanning position. For example, the incremental motion information of the subject may include initial position information of the subject and continuous incremental speed of the subject. For example, at the beginning of scanning, a scanning position of the subject corresponds to a real crystal C1 and the continuous incremental speed of the subject is s1 per second, the scanning position of the subject corresponding to the real crystal C1 in the receiving time may be obtained according to the receiving time of the γ-photon and the above-mentioned continuous incremental speed.

From the above descriptions, the virtual PET system 10 may be constructed. The scanning in the continuous incremental scanning mode may be equivalent to a scanning in which the subject is fixed in the virtual PET system 10 for a period of time. Also, in the scanning process, the single-photon count of each of the virtual crystals in the virtual PET system 10 may also be obtained by the above-mentioned method.

An example of obtaining a crystal receiving efficiency for a real crystal is provided below, and detailed description may not be limited to the following illustrated method. When N single-photons are emitted to a real crystal in unit time and M single photons among them are identified, the crystal receiving efficiency for the real crystal is η=M/N.

In an example, the crystal receiving efficiency for each of the real crystals in the PET system may be an approximate value. A cylindrical water phantom may be placed at the center of the PET system, and pharmaceutical activity in the cylindrical water phantom ensures that a dose in the PET system is close to that in the process of scanning the subject. The cylindrical water phantom may be scanned with the scanning bed kept stationary to obtain the single-photon counting rates for all real crystals, and the crystal receiving efficiency for a real crystal is obtained by the following formula:

$$\eta_i = \frac{S_i}{\bar{S}}. \qquad (1)$$

Where, i represents a crystal number of a real crystal; $S_i$ may represent the single-photon counting rate for the real crystal i; and $\bar{S}$ may represent a mean value of the single-photon counting rates for all the real crystals.

As can be seen from the above analysis, under the same dose, a ratio between the single-photon counting rate for the real crystal and the mean value of the single-photon counting rates for all real crystals may be obtained, and the obtained ratio may be taken as the crystal receiving efficiency for the real crystal.

However, in practice, the crystal receiving ratio for the real crystal may vary at different pharmaceutical activities. To obtain the crystal receiving efficiency for the real crystal more accurately, in another example, the crystal receiving efficiency for each of the real crystals under different doses corresponding to different pharmaceutical activities may be obtained. According to the data under different doses, a function relative accurately indicating a relationship between single-photon counting rate for the real crystal and crystal receiving efficiency for the real crystal may be established. Thus, after the single-photon counting rate for the real crystal is obtained, the corresponding crystal receiving efficiency may be obtained according to the function. It may be seen from the above analysis that the crystal receiving efficiency for the real crystal may be obtained according to the single-photon counting rate for the real crystal and the function indicating a relationship between single-photon counting rate and crystal receiving efficiency, where the function may be obtained according to the single-photon counting rate and the crystal receiving efficiency that are obtained by tests under different doses.

For example, to obtain the crystal receiving efficiency for each of the real crystals in the PET system under a pharmaceutical activity, a cylindrical water phantom having an axial length greater than that of the PET system may be placed at the center of the PET system. A pharmaceutical dose in the cylindrical water phantom may be represented by Do. The cylindrical water phantom may be scanned with the scanning bed kept stationary. In this way, the single-photon counting rates for all real crystals may be obtained. The crystal receiving efficiency for a real crystal under the dose Do may be obtained by using the following formula:

$$\eta_i(0) = S_i(0)/\bar{S}(0) \qquad (2).$$

Where, i may represent a crystal number for the real crystal; $S_i(0)$ may represent the single-photon counting rate for the real crystal i; $\overline{S}(0)$ may represent a mean value of the single-photon counting rates for all real crystals; $\eta_i(0)$ may represent the crystal receiving efficiency for the real crystal i under dose Do.

In addition, to obtain the crystal receiving efficiency for each of the real crystals in the PET system under different doses, as mentioned above, a cylindrical water phantom having an axial length greater than that of the PET system is placed at the center of the PET system, and a pharmaceutical dose in the cylindrical water phantom may be represented by $D_t$. The cylindrical water phantom is scanned with the scanning bed kept stationary. In this way, the single-photon counting rates for all real crystals may be obtained. The crystal receiving efficiency $\eta_i(t)$ for a real crystal under the dose $D_t$ may be obtained by using the following formula:

$$\eta_i(t) = \eta_i(0)\frac{s_i(t)/D_t}{s_i(0)/D_0}. \quad (3)$$

Where, $\eta_i(t)$ may be obtained by testing different dose $D_t$ as described above.

On this basis, a function $\eta_i(t)$ may be established according to the test results under different doses. The function may be used to represent a relationship between the single-photon counting rate $S_i(t)$ for a real crystal and the crystal receiving efficiency $\eta_i(t)$ for the real crystal. In this way, if the single-photon counting rate $S_i(t)$ for the real crystal is obtained, the crystal receiving efficiency for the real crystal may be obtained.

Crystal receiving efficiency for a real crystal in the real PET system may be obtained according to the above-mentioned method. After the crystal receiving efficiency for the real crystal is obtained, crystal receiving efficiency for other real crystals in the PET system may be obtained conveniently and rapidly.

In an example, a single-photon counting rate for each of the real crystals under different activities within a clinical activity range may vary. With the activities increasing, the single-photon counting rates for all real crystals may increase. Under a dose $D_t$, a proportional relationship between single-photon counting rates $S_i(t)$ for different real crystals may be constant. Therefore, as long as the single-photon counting rate for a real crystal is obtained, the single-photon counting rates for all real crystals may be obtained based on the constant proportional relationship. Also, if a mean value of the single-photon counting rates for several real crystals is obtained, the single-photon counting rates for all real crystals may be obtained based on the constant proportional relationship as well. That is, as long as the single-photon counting rate for a real crystal or a mean value of the single-photon counting rates for several real crystals is obtained, the single-photon counting rates for all real crystals may be obtained based on the constant proportional relationship. Then, according to the above-mentioned function indicating relationship between the single-photon counting rate and the crystal receiving efficiency, the corresponding crystal receiving efficiency for a real crystal may be obtained.

For example, the proportional relationship between the single-photon counting rates for the real crystal 1 and the real crystal 2 is 1:2; the proportional relationship between the single-photon counting rates for the real crystal 2 and the real crystal 3 is 1:2; and the proportional relationship between the single-photon counting rates for the real crystal 3 and the real crystal 4 is 1:2. Based on this, assuming that the single-photon counting rate for the real crystal 2 is A, the single-photon counting rate for the real crystal 1 may be A/2, and the single-photon counting rate for the real crystal 3 may be A*2 and the single-photon counting rate for the real crystal 4 may be A*4. In another example, assuming that the mean value of the single-photon counting rates for the above four real crystals is B, the sum of the single-photon counting rates for the four real crystals is 4B; thus, the single-photon counting rate for the real crystal 1 may be 4B/15, and the single-photon counting rate for the real crystal 2 may be 8B/15, the single-photon counting rate for the real crystal 3 may be 16B/15, and the single-photon counting rate for the real crystal 4 may be 32B/15.

To obtain the crystal receiving efficiency according to the single-photon counting rate for a real crystal, the single-photon counting rate for the real crystal may be first obtained. In an example, for each of the real crystals, a number of single-photons received by the real crystal may be obtained, and the single-photon counting rate for the real crystal may be obtained according to the number of single-photons and time for receiving the single-photons. For example, the single-photon counting rate for the real crystal may be obtained by dividing the number of single-photons received by the real crystal by the receiving time.

In another example, a plurality of single-photon counting components corresponding to a scanning position may be obtained. As noted above, the number of single-photons received by a real crystal in a case of corresponding to a scanning position is referred to as a single-photon counting component. A single-photon counting rate for a virtual crystal associated with the scanning position may be obtained according to the plurality of single-photon counting components. A single-photon counting rate for a real crystal associated with the virtual crystal may be obtained according to the single-photon counting rate for the virtual crystal.

Regarding the process of obtaining a single-photon counting rate for a real crystal according to single-photon counting rate for a virtual crystal, it may be seen from above that the single-photon count of the virtual crystal 11 is obtained by accumulating the number of single-photons received by each of the real crystals in the crystal string from the real crystal 53 to the real crystal 58 when each of the real crystals relatively moves to the scanning position 13. Thus, the single-photon count of a virtual crystal may be the sum of the single-photon counts of a plurality of real crystals, and the single-photon counting rate for a virtual crystal is the sum of the single-photon counting rates for a plurality of real crystals. Assuming that the single-photon counting rate for the virtual crystal 11 is C, it may indicate that the sum of the single-photon counting rates for the plurality of real crystals from the real crystal 53 to the real crystal 58 is C, and then the single-photon counting rate for any one real crystal from the real crystal 53 to the real crystal 58 may be obtained based on the proportional relationship between the single-photon counting rates for the real crystals from the real crystal 53 to the real crystal 58.

Due to a high noise level of delay random coincidence data, random coincidence data may be obtained by performing a denoising process for the delay random coincidence data. Before describing the process for denoising delay random coincidence data, the random coincidence data may be described first.

The random coincidence data in the present disclosure may be obtained by denoising the delay random coincidence data. The denoised random coincidence data can be the random coincidence data on a response line. The response line may be a line connecting two virtual crystals that obtain coincidence data. In an example, random coincidence data on the response line=random coincidence counting rate for the response line*scanning time for the response line (4).

Figure 9:
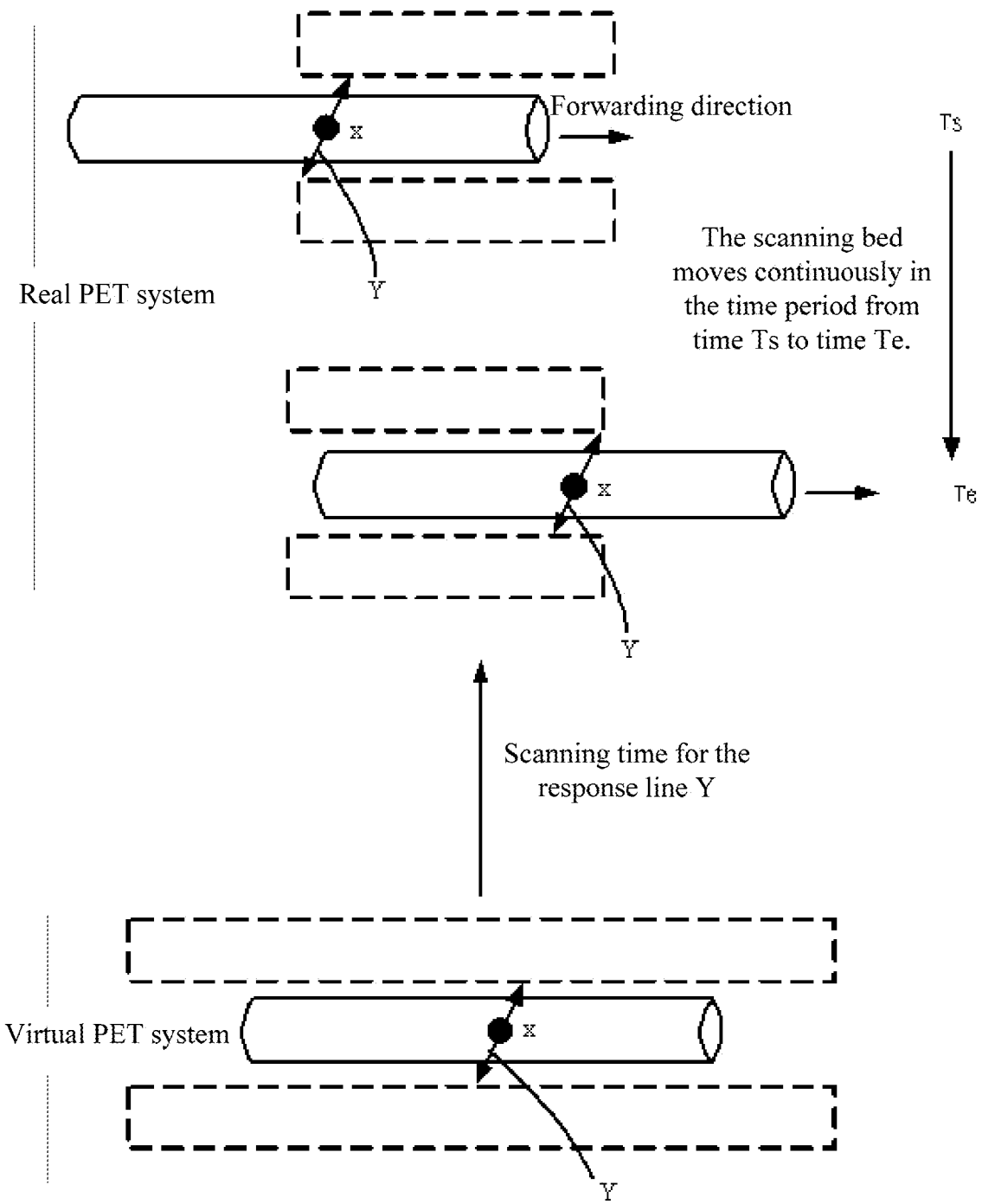
FIG. 9 is a schematic diagram of scanning time for a response line according to one or more examples of the present disclosure.

Assuming that a response line associated with the virtual crystal i and the virtual crystal j in the virtual PET system, in the above formula, the random coincidence counting rate for the response line may be a number of random coincidence events obtained by the virtual crystal i and the virtual crystal j in unit time, and the scanning time may be the scanning time for the response line in the real PET system, which may be referred to as the scanning time for the response line. For example, the above "scanning time for the response line" may be illustrated in conjunction with FIG. 9. In FIG. 9, the response line Y in the virtual PET system may correspond to a scanning position x on the subject. In the real PET system, a time period from beginning of scanning to finishing of scanning, i.e., the time period from time Ts to time Te, is the scanning time corresponding to the response line Y. An example of obtaining a random coincidence counting rate for a response line may be provided as follows, and detailed description may not be limited to the following illustrated method.

In an example, the random coincidence counting rate for the response line associated with the virtual crystal i and the virtual crystal j may be obtained by the following method. For each of the virtual crystals, the random coincidence counting rate for the response line may be obtained according to the single-photon counting rates for the two virtual crystals associated with the response line and the crystal receiving efficiency for each of the real crystals associated with the two virtual crystals on the response line.

The following formula (5) is a formula for obtaining the random coincidence counting rate for the response line associated with the virtual crystal i and the virtual crystal j. The following will illustrate the deduction process of the formula (5) and the meaning of the formula (5) to describe the above-mentioned method of obtaining the random coincidence counting rate for the response line.

$$r_{ij} = \frac{2\tau}{m}(\eta_{ix1}\bar{s}_i\eta_{jy1}\bar{s}_j + \eta_{ix2}\bar{s}_i\eta_{jy2}\bar{s}_j + \ldots + \eta_{ixm}\bar{s}_i\eta_{jym}\bar{s}_j) \quad (5)$$
$$= \frac{2\tau}{m}(\eta_{ix1}\eta_{jy1} + \eta_{ix2}\eta_{jy2} + \ldots + \eta_{ixm}\eta_{jym})\bar{s}_i\bar{s}_j$$

Figure 10:
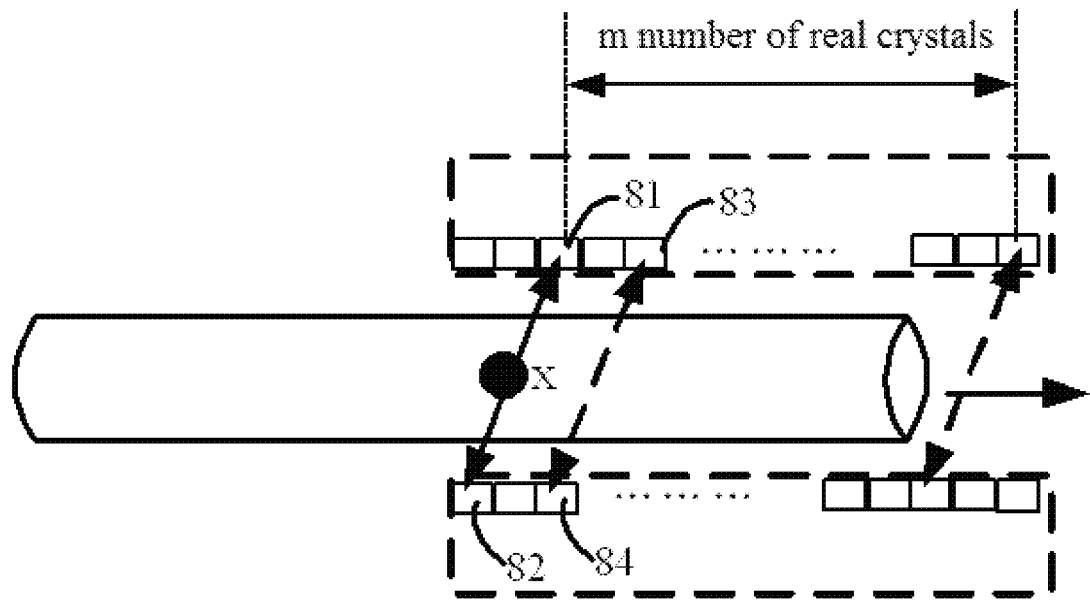
FIG. 10 is a schematic diagram of a response line scanning crystal according to one or more examples of the present disclosure.

When the response line Y scans in the real PET system shown in FIG. 9, the response line Y may pass through m number of pairs of real crystals as shown in FIG. 10. FIG. 10 illustrates a scanning process of the response line. A solid response line may represent a starting scanning point of the response line, and two dotted lines of response may represent two positions of the response line in the scanning process, and the whole scanning process may pass through m number of pairs of real crystals. For example, in the direction of along a response line, a real crystal 81 and a real crystal 82 form a pair of crystals, while a real crystal 83 and a real crystal 84 form another pair of crystals, and there are m number of pairs of real crystals in total. Moreover, the real crystals in the pairs of real crystals that the response line passes through in the scanning process may be referred to as each of the real crystals associated with the virtual crystals on the response line. For example, each of the real crystals associated with the virtual crystal i on the response line may include the real crystal 81, the real crystal 83 and the like.

In the formula (5), i and j are numbers of two virtual crystals on the response line; x1, x2, . . . , xm may represent each of the real crystals associated with the virtual crystal i on the response line; y1, y2, . . . , ym may represent each of the real crystals associated with the virtual crystal j on the response line; $\eta_{ix1}$, $\eta_{ix2}$, . . . , $\eta_{ixm}$, are respective crystal receiving efficiencies corresponding to real crystals x1, x2, . . . , xm; $\eta_{jy1}$, $\eta_{jy2}$, . . . , $\eta_{jym}$ are respective crystal receiving efficiencies corresponding to real crystals y1, y2, . . . , ym; $\bar{s}_i$ represents a single-photon counting rate emitted from the subject to the virtual crystal i; $\bar{s}_j$ represents a single-photon counting rate emitted from the subject to the virtual crystal j; and 2 τ is the coincidence time window. It may be difficult to obtain the single-photon counting rates emitted from the subject to the virtual crystal i and the virtual crystal j.

The above has described that each of the virtual crystals may be associated with a plurality of real crystals. For example, a virtual crystal 1 may be associated with a real crystal 1, a real crystal 2 and a real crystal 3; a virtual crystal 6 may be associated with a real crystal 7, a real crystal 8 and a real crystal 9. Based on this, assuming that at a first scanning position, the virtual crystal 1 is associated with the real crystal 1, and virtual crystal 6 is associated with the real crystal 7; at a second scanning position, the virtual crystal 1 is associated with the real crystal 2, and the virtual crystal 6 is associated with the real crystal 8; and at a third scanning position, the virtual crystal 1 is associated with the real crystal 3, and the virtual crystal 6 is associated with the real crystal 9. For the formula (5), when i is 1 and j is 6, the number m of the pairs of real crystals is 3; x1 may be the real crystal 1, x2 may be the real crystal 2, x3 may be the real crystal 3, y1 may be the real crystal 7, y2 may be the real crystal 8, and y3 may be the real crystal 9.

In the formula (5), it may be given:

$$\alpha_{ij} = \frac{\eta_{ix1}\eta_{jy1} + \eta_{ix2}\eta_{jy2} + \ldots + \eta_{ixm}\eta_{jym}}{m}. \quad (6)$$

Where, $\alpha_{ij}$ is crystal pair receiving efficiency for the virtual crystal i and the virtual crystal j.

On this basis, the formula (5) may be simplified as:

$$r_{ij}=2\tau T\alpha_{ji}\bar{s}_i\bar{s}_j \quad (7).$$

After the random coincidence counting rate $r_{ij}$ for the response line is obtained, as the random coincidence data for the response line is equal to random coincidence counting rate*scanning time, the random coincidence data for the response line may be as follow:

$$R_{ij}=2\tau T\alpha_{ji}\bar{s}_i\bar{s}_j \quad (8).$$

Where, T is the scanning time corresponding to the response line, and $R_{ij}$ is the random coincidence data for the response line.

Based on the above analysis, random coincidence data $2\tau T\alpha_{ij}\bar{s}_i\bar{s}_j$ is the result of denoising the delay random coincidence data in the present disclosure.

As it is difficult to obtain the single-photon counting rates emitted from the subject to the virtual crystal i and the virtual crystal j, it may also be difficult to obtain the random coincidence data for the response line by $R_{ij}=2\Sigma T\alpha_{ij}\bar{s}_i\bar{s}_j$. To obtain relatively accurate random coincidence data, a plurality of pieces of delay random coincidence data may be used, where the delay random coincidence data may be obtained by using the delay coincidence window. Relatively accurate random coincidence data may be obtained by denoising the delay random coincidence data.

Figure 11:
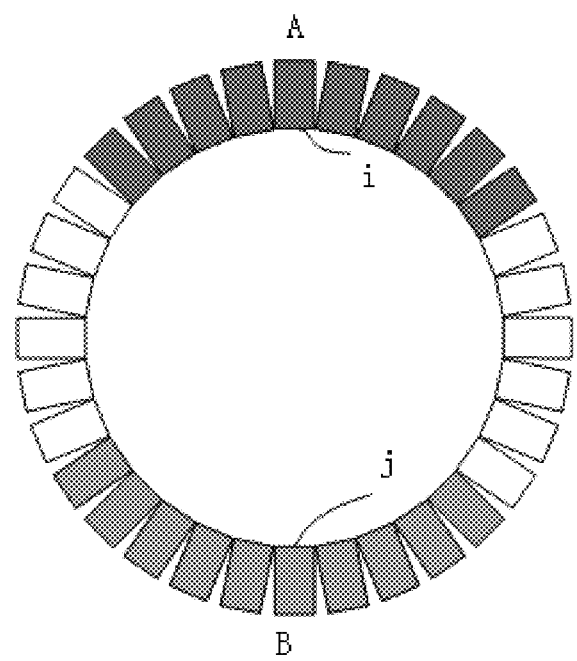
FIG. 11 is a schematic diagram of two continuous crystal blocks according to one or more examples of the present disclosure.

In an example, delay random coincidence data $\overline{R}_{ij}$ is the delay random coincidence data for the virtual crystal i and the virtual crystal l, l∈B, and set B is a set of virtual crystals including virtual crystal j. Delay random coincidence data $\overline{R}_{jk}$ is the delay random coincidence data for the virtual crystal j and the virtual crystal k, k∈A, and set A is a set of virtual crystals including virtual crystal i. $\overline{R}_{lk}$ is the delay random coincidence data for the virtual crystal l and the virtual crystal k. Where, as shown in FIG. 11, the virtual crystal sets A and B may respectively indicate two opposite continuous Blocks in a detector ring. Any of the crystals in set A and any of the crystals in set B may be paired to form a response line.

To determine the virtual crystal set A and the virtual crystal set B, in an example, the number of virtual crystals in set A and the number of virtual crystals in set B may be given. Under normal circumstances, the number of virtual crystals in set A is the same as the number of virtual crystals in set B. Assuming that the number of virtual crystals in set A is H, the number of virtual crystals in set B may be also H. As shown in FIG. 11, the number H may be 10. Also, the virtual crystals in set A are continuous and the virtual crystals in set B are also continuous. On this basis, as long as the set A includes the virtual crystal i and the set B includes the virtual crystal j, it may be determined that the set A includes continuous H virtual crystals of which one is the virtual crystal i and the set B includes continuous H virtual crystals of which one is the virtual crystal j.

In an example, the virtual crystal i may be located in the middle of the continuous H virtual crystals. For example, if H/2 is an integer, the virtual crystal i is the H/2 virtual crystal in the set A; if H/2 is a decimal, the virtual crystal i is the round up to H/2 virtual crystal in the set A. Similarly, the virtual crystal j is the H/2 virtual crystal in the set B or the round up to H/2 virtual crystal in the set B.

In an example, the virtual crystal i and the virtual crystal j may also be in other positions. For example, the virtual crystal i may be the first virtual crystal, the last virtual crystal or the like in the set A, and the virtual crystal j may be the first virtual crystal, the last virtual crystal or the like in the set B. The positions of the virtual crystal i and the virtual crystal j will not be illustrated in examples of the present disclosure as long as the set A and the set B may be obtained.

It may be noted that the delay random coincidence data for a real crystal may be obtained by the above-mentioned delay coincidence window, Therefore, the delay random coincidence data for a virtual crystal may be obtained according to the delay random coincidence data for real crystals. In an example, all the real crystals associated with each of the virtual crystals may be determined, and the delay random coincidence data for two virtual crystals on a response line may be obtained according to the delay random coincidence data for real crystals associated with the virtual crystals. For example, a virtual crystal 1 may be associated with a real crystal 1, a real crystal 2 and a real crystal 3. A virtual crystal 2 may be associated with a real crystal 4, a real crystal 5 and a real crystal 6. The delay random coincidence data associated with the virtual crystal 1 and the virtual crystal 2 on the response line may be: the delay random coincidence data for the real crystal 1 and the real crystal 4 plus the delay random coincidence data for the real crystal 2 and the real crystal 5 plus the delay random coincidence data for the real crystal 3 and the real crystal 6.

For example, when i is 11 and j is 16, the set B of virtual crystals may include a virtual crystal 15, a virtual crystal 16 and a virtual crystal 17, and the set A of virtual crystals may include a virtual crystal 10, a virtual crystal 11 and a virtual crystal 12. On this basis, k may be 10, 11 or 12, and l may be 15, 16 or 17. When k is 12 and l is 17, $\overline{R}_{ij}$ is the delay random coincidence data for the virtual crystal 11 and the virtual crystal 17, $\overline{R}_{jk}$ is the delay random coincidence data for the virtual crystal 16 and the virtual crystal 12, and $\overline{R}_{lk}$ is the delay random coincidence data for the virtual crystal 17 and the virtual crystal 12. For other combinations of values of k and l, there will be corresponding delay random coincidence data $\overline{R}_{il}$, $\overline{R}_{jk}$, and $\overline{R}_{lk}$, which are not redundantly described herein.

In an example, random coincidence data $R_{il}$ may be obtained according to the following formula:

$$R_{il} = T(2\tau\alpha_{il}\overline{s}_i\overline{s}_l) \qquad (9).$$

The random coincidence data $R_{jk}$ may be obtained according to the following formula:

$$R_{jk} = T(2\tau\alpha_{jk}\overline{s}_j\overline{s}_k) \qquad (10).$$

The random coincidence data $R_{lk}$ may be obtained according to the following formula:

$$R_{lk} = T(2\tau\alpha_{lk}\overline{s}_l\overline{s}_k) \qquad (11).$$

Further, due to l∈B and k∈A, $R_{iB}$ may be obtained according to the following formula:

$$R_{iB} = \Sigma_{l \in B} R_{il} = T(2\tau\Sigma_{l \in B}\alpha_{il}\overline{s}_i\overline{s}_l) \qquad (12).$$

Similarly, $R_{jA}$ may be obtained according to the following formula:

$$R_{jA} = \Sigma_{k \in A} R_{jk} = T(2\tau\Sigma_{k \in A}\alpha_{jk}\overline{s}_j\overline{s}_k) \qquad (13),$$

On this basis, a formula (14) may be obtained:

$$R_{iB} * R_{jA} = T(2\tau\Sigma_{l \in B}\alpha_{il}\overline{s}_i\overline{s}_l) * T(2\tau\Sigma_{k \in A}\alpha_{jk}\overline{s}_j\overline{s}_k) \qquad (14).$$

The formula (14) may be rearranged to obtain:

$$R_{iB} * R_{jA} = 2\tau T \alpha_{ij}\overline{s}_i\overline{s}_j \left( 2\tau T \sum_{l \in B} \sum_{k \in A} \frac{\alpha_{il}\alpha_{jk}}{\alpha_{ij}\alpha_{lk}} \alpha_{lk}\overline{s}_l\overline{s}_k \right). \qquad (15)$$

As $R_{ij}$ is $2\tau T\alpha_{ij}\overline{s}_i\overline{s}_j$, and $R_{lk}$ is $T(2\tau\alpha_{lk}\overline{s}_l\overline{s}_k)$, the formula (15) may be rearranged to obtain:

$$R_{iB} * R_{jA} = R_{ij} \sum_{l \in B} \sum_{k \in A} \frac{\alpha_{il}\alpha_{jk}}{\alpha_{ij}\alpha_{lk}} R_{lk}. \qquad (16)$$

Further, the formula (16) may be rearranged to obtain:

$$R_{ij} = \frac{R_{iB} * R_{jA}}{\sum_{l \in B} \sum_{k \in A} \frac{\alpha_{il}\alpha_{jk}}{\alpha_{ij}\alpha_{lk}} R_{lk}}. \qquad (17)$$

Then, the above-mentioned $R_{iB}$ and $R_{jA}$ may be substituted into the formula (17) to obtain:

$$R_{ij} = \frac{\sum_{l \in B} R_{il} * \sum_{k \in A} R_{jk}}{\sum_{l \in B} \sum_{k \in A} \frac{\alpha_{il}\alpha_{jk}}{\alpha_{ij}\alpha_{lk}} R_{lk}} = \frac{\sum_{l \in B} \overline{R}_{il} * \sum_{k \in A} \overline{R}_{jk}}{\sum_{l \in B} \sum_{k \in A} \frac{\alpha_{il}\alpha_{jk}}{\alpha_{ij}\alpha_{lk}} \overline{R}_{lk}}. \qquad (18)$$

Where, $R_{ij}$ is the denoised random coincidence data. It may be noted that after random coincidence data $R_{il}$, $R_{jk}$, $R_{lk}$ are replaced by the delay random coincidence data $\overline{R}_{il}$, $\overline{R}_{jk}$, $\overline{R}_{lk}$, $R_{ij}$ may be estimated with the delay random coincidence data of many virtual crystals in the set A and the set B, thereby effectively reducing the noise level.

In the above formulas, $\alpha_{il}$ is the crystal pair receiving efficiency for the virtual crystal i and the virtual crystal l; $\alpha_{jk}$ is the crystal pair receiving efficiency for the virtual crystal j and the virtual crystal k; and $\alpha_{lk}$ is the crystal pair receiving efficiency for the virtual crystal l and the virtual crystal k. For example, when i is 11, j is 16, k is 12 and l is 17, $\alpha_{ij}$ is the crystal pair receiving efficiency for the virtual crystal 11 and the virtual crystal 17, $\alpha_{jk}$ the crystal pair receiving efficiency for the virtual crystal 16 and the virtual crystal 12, and $\alpha_{lk}$ the crystal pair receiving efficiency for the virtual crystal 17 and the virtual crystal 12.

The formula for obtaining $\alpha_{ij}$ is similar to that for obtaining $\alpha_{ij}$ with only j in $\alpha_{ij}$ being replaced by l, for example:

$$\alpha_{il} = \frac{\eta_{ix1}\eta_{ly1} + \eta_{ix2}\eta_{ly2} + \ldots + \eta_{ixm}\eta_{lym}}{m}. \quad (19)$$

The formula for obtaining $\alpha_{jk}$ is similar to that for obtaining $\alpha_{ij}$ as shown above with only j in $\alpha_{ij}$ being replaced by k and i in $\alpha_{ij}$ being replaced by j; also, the formula for obtaining $\alpha_{lk}$ is similar to that for obtaining $\alpha_{ij}$ as shown above with only j in $\alpha_{ij}$ being replaced by k and i in $\alpha_{ij}$ being replaced by l, which are not redundantly described herein.

Figure 12:
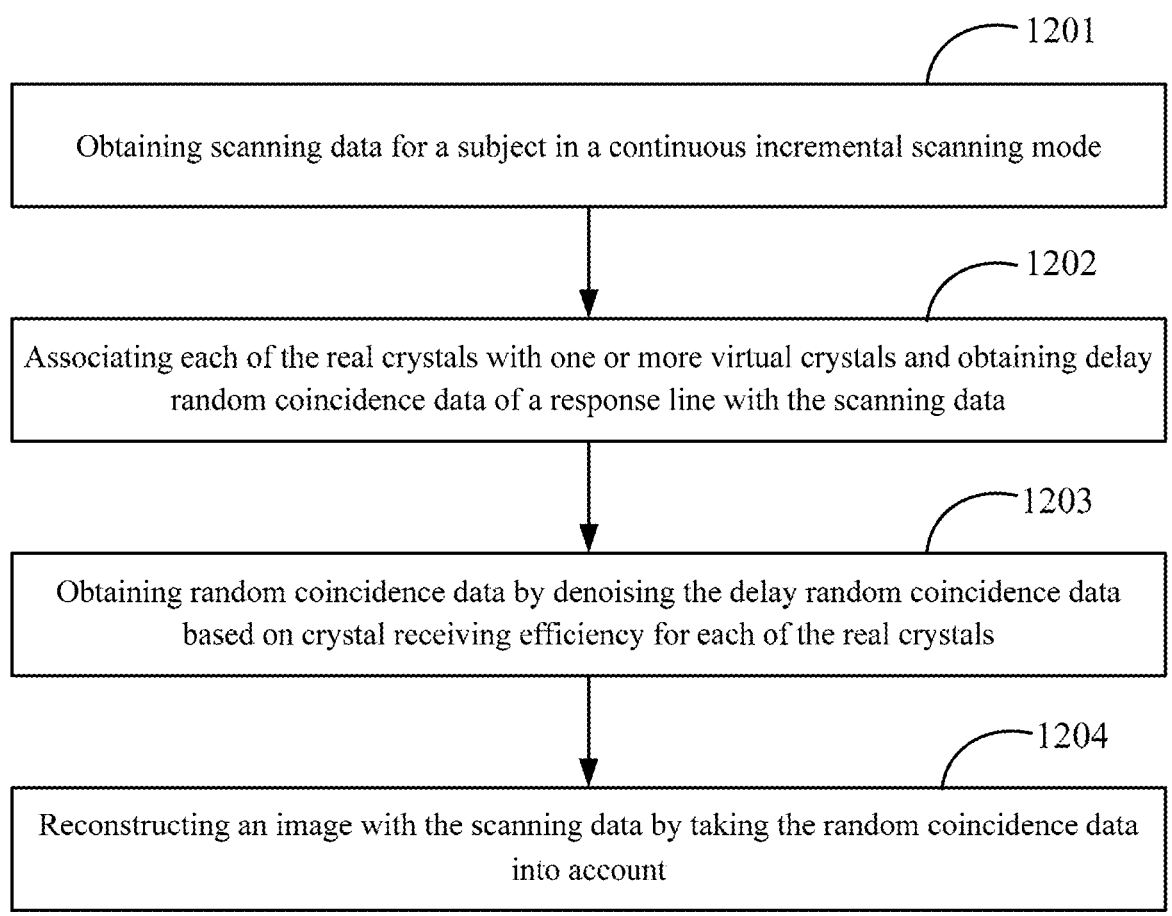
FIG. 12 is a flow diagram of a method of reconstructing image according to one or more examples of the present disclosure.

From the above descriptions, a method of reconstructing image in an example of the present disclosure may be applied to medical equipment including a plurality of real crystals, and may include steps 1201 to 1204 shown in FIG. 12.

At step 1201, scanning data for a subject in a continuous incremental scanning mode may be obtained. In the continuous incremental scanning mode, radioactive nuclides in the subject may release positrons e+ in their decay process. When a positron e+ meets a negatron e− in the subject, a positron annihilation event may occur. The positron annihilation event may generate two γ-photons. The real crystals may receive the γ-photons, and the receiving information (e.g., receiving time, receiving position and the like) of the γ-photons is the scanning data. Certainly, the scanning data may also include other information. All data obtained in the scanning process in the continuous incremental scanning mode may be regarded as the scanning data, which is not redundantly described herein.

At step 1202, a real crystal may be associated with one or more virtual crystals and delay random coincidence data of a response line may be obtained according to the scanning data.

At this step 1202, the above process has described that the real crystal may be associated with one or more virtual crystals so as to form a virtual PET system, and a correspondence between the real crystal and the virtual crystal may be determined according to the information of the real crystal position and a scanning position, which is not redundantly described herein.

At this step 1202, the above process has described that delay random coincidence data for the real crystal may be obtained by using a delay coincidence window according to the scanning data. Besides, for two virtual crystals, delay random coincidence data for the two virtual crystals may be obtained according to delay random coincidence data for all real crystals associated with the two virtual crystals, which is not redundantly described herein.

At step 1203, random coincidence data may be obtained by denoising the delay random coincidence data based on crystal receiving efficiency for each of the real crystals.

In an example, before the step 1203, a single-photon counting rate for each of the real crystals may be also obtained, and the crystal receiving efficiency for the real crystal may be obtained according to the single-photon counting rate for the real crystal.

In an example, obtaining the single-photon counting rate for each of the real crystals may include the following methods.

Method 1 is, a number of single-photons received by the real crystal may be obtained, and the single-photon counting rate for the real crystal may be obtained according to the number of single-photons and time for receiving the single-photons.

Method 2 is, a plurality of single-photon counting components corresponding to a scanning position of the subject may be obtained; a number of single-photons received by a virtual crystal associated with the scanning position may be obtained according to the plurality of single-photon counting components; a single-photon counting rate for the virtual crystal may be obtained according to the number of single-photons received by the virtual crystal and scanning time corresponding to the scanning position; and the single-photon counting rate for each of the real crystals associated with the virtual crystal may be obtained according to the single-photon counting rate for the virtual crystal.

As a virtual crystal is associated with a scanning position of the subject, the number of single-photons received by each of the real crystals associated with the virtual crystal may be accumulated to the virtual crystal. Each of the single-photon counting components is a number of single-photons received by a real crystal associated with the virtual crystal when the scanning position moves to the corresponding real crystal and the real crystal and the virtual crystal have the same relative position relationship with the scanning position.

When obtaining a single-photon counting rate for the virtual crystal associated with the scanning position according to the plurality of single-photon counting components, the scanning position of the subject corresponding to a single-photon may be determined according to incremental motion information of the subject and time for receiving the single-photon; the number of single-photons received by the virtual crystal may be obtained by accumulating the plurality of single-photon counting components to the virtual crystal associated with the scanning position; and the single-photon counting rate for the virtual crystal may be obtained according to the number of single-photons received by the virtual crystal and scanning time corresponding to the scanning position in the scanning process.

In an example, obtaining the crystal receiving efficiency for the real crystal according to the single-photon counting rate for the real crystal may include: under different doses, obtaining the crystal receiving efficiency for the real crystal according to the single-photon counting rate for the real crystal and a function indicating relationship between single-photon counting rate and crystal receiving efficiency for the real crystal, wherein the function is obtained according to the crystal receiving efficiency obtained under different doses; or, under the same dose, obtaining a ratio between the single-photon counting rate for the real crystal and a mean value of the single-photon counting rates for all the real crystals as the crystal receiving efficiency.

In an example, obtaining the random coincidence data by denoising the delay random coincidence data according to the crystal receiving efficiency for the real crystal may include: determining two virtual crystals on the response line and each of the real crystals associated with the two virtual crystals on the response line, and obtaining crystal receiving efficiency for each of the determined real crystals; obtaining crystal pair receiving efficiency for the two virtual crystals according to the crystal receiving efficiency for each of the determined real crystals, and obtaining the random coincidence data by denoising the delay random coincidence data according to the crystal pair receiving efficiency.

In an example of the present disclosure, obtaining the crystal pair receiving efficiency for the two virtual crystals according to the crystal receiving efficiency for each of the determined real crystals may include: assuming that the two virtual crystals are virtual crystal i and virtual crystal j on the response line, and obtaining the crystal pair receiving efficiency for the virtual crystal i and the virtual crystal j according to the crystal receiving efficiency for m number of real crystals associated with the virtual crystal i on the response line and the crystal receiving efficiency for m number of real crystals associated with the virtual crystal j on the response line.

In an example, the crystal pair receiving efficiency for the two virtual crystals may be obtained according to the following formula:

$$\alpha_{ij} = \frac{\eta_{ix1}\eta_{jy1} + \eta_{ix2}\eta_{jy2} + \ldots + \eta_{ixm}\eta_{jym}}{m}.$$

The contents of this formula may be referred to the above examples.

In an example, obtaining the random coincidence data by denoising the delay random coincidence data according to the crystal pair receiving efficiency may include: assuming that the virtual crystal i belongs to a set A including m number of virtual crystals, and the virtual crystal j belongs to a set B including m number of virtual crystals; and obtaining the random coincidence data for the virtual crystal i and the virtual crystal j by denoising delay random coincidence data for the virtual crystal i and the virtual crystal l among the set B, delay random coincidence data for the virtual crystal j and the virtual crystal k among the set A and delay random coincidence data for the virtual crystal l and virtual crystal k, according to crystal pair receiving efficiency for the virtual crystal i and the virtual crystal l, crystal pair receiving efficiency for the virtual crystal j and the virtual crystal k and crystal pair receiving efficiency for the virtual crystal l and virtual crystal k, wherein i, j, k and l are non-negative integers.

In an example, the delay random coincidence data may be denoised according to the following formula:

$$R_{ij} = \frac{\sum_{l \in B} \overline{R}_{il} * \sum_{k \in A} \overline{R}_{jk}}{\sum_{l \in B} \sum_{k \in A} \frac{\alpha_{il}\alpha_{jk}}{\alpha_{ij}\alpha_{lk}} \overline{R}_{lk}}.$$

The contents of this formula may be referred to the above examples.

At block 1204, an image may be reconstructed with the scanning data by taking the random coincidence data into account.

Where, the scanning data may be processed according to the random coincidence data and the image may be reconstructed according to the processed scanning data. For example, during reconstructing the image, the random coincidence data may be eliminated or as a factor for reconstructing the image. For each response line, the denoised relay random coincidence data for the response line may be used when reconstructing the image, such that the data for reconstructing the image is more accurate.

Based on the above-described technical solutions, in examples of the present disclosure, the delay random coincidence data may be denoised according to the crystal receiving efficiency for each of the real crystals to obtain the random coincidence data. The scanning data may be processed according to the random coincidence data, and the processed scanning data may be used for reconstructing image so as to improve the quality of the reconstructed image.

Figure 13:
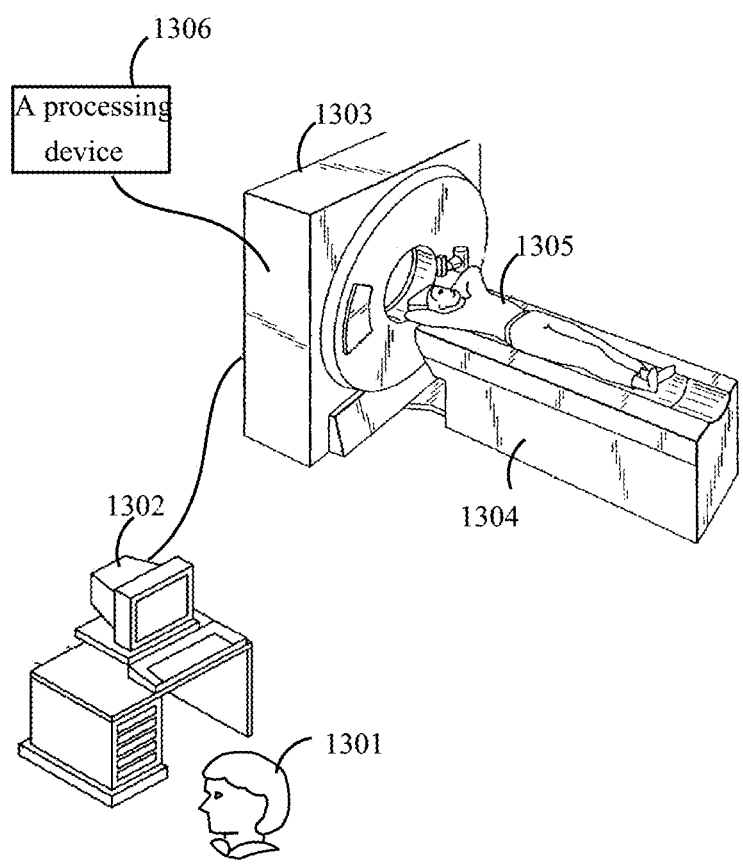
FIG. 13 is a schematic diagram of a scanning scenario according to one or more examples of the present disclosure.

FIG. 13 illustrates an application scenario in which a subject is scanned. For example, the subject may be scanned in a continuous incremental scanning mode. An operator 1301 may operate a detecting device 1303 including a plurality of real crystals by a control console 1302 such that the subject 1305 on a scanning bed 1304 is scanned in the continuous incremental scanning mode. In the scanning process, each of the real crystals in the detecting device 1303 may transmit the number of received single-photons to a backend processing device 1306. The processing device 1306 may be a device for processing the data received by the detecting device and reconstructing the image. The processing device 1306 may execute the method of reconstructing the image as described in the above method examples. For example, the control console 1302, the detecting device 1303, the processing device 1306 may be functional modules within the medical equipment.

Figure 14:
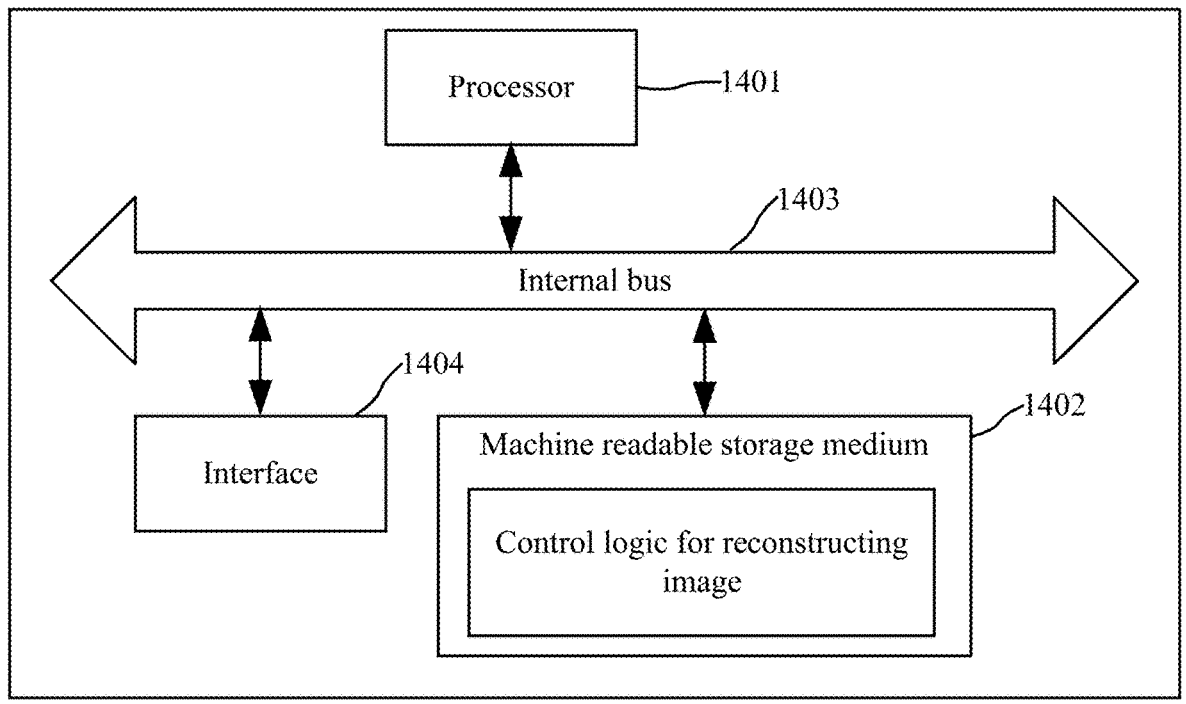
FIG. 14 is a hardware architecture diagram of a device for reconstructing image according to one or more examples of the present disclosure.

The present disclosure also provides a device for reconstructing image. The device may be applied to medical equipment including a plurality of real crystals. FIG. 14 is a hardware architecture diagram of a device for reconstructing the image according to an example. Referring to FIG. 14, the device for reconstructing the image may include a processor 1401 and a machine readable storage medium 1402. The processor 1401 and the machine readable storage medium 1402 are typically connected to each other by an internal bus 1403. In other possible implementations, the device may also include an external interface 1404 for communicating with other equipment or components.

In different examples, the machine readable storage medium 1402 may be a Read-Only Memory (ROM), a volatile memory, a nonvolatile memory, a flash memory, memory drive (such as a hard disk drive), a solid state disk, any type of memory disc (such as CD, DVD and the like), or a similar storage medium, or a combination thereof.

Figure 15:
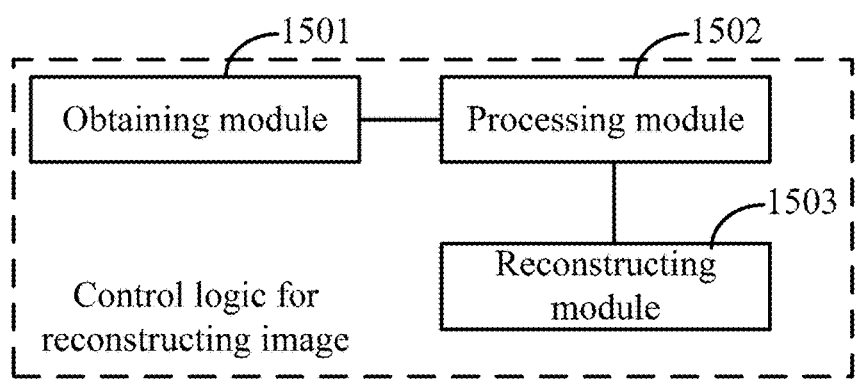
FIG. 15 is a block diagram of control logic for reconstructing image according to one or more examples of the present disclosure.

Further, control logic for reconstructing image may be stored on the machine readable storage medium 1402. As shown in FIG. 15, divided by functions, the control logic for reconstructing the image may include: an obtaining module 1501, a processing module 1502 and a reconstructing module 103.

The obtaining module 1501 may be configured to obtain scanning data for a subject in a continuous incremental scanning mode; and associate a real crystal with one or more virtual crystals, and obtain delay random coincidence data of a response line according to the scanning data.

The processing module 1502 may be configured to denoise the delay random coincidence data according to crystal receiving efficiency for each of the real crystals to obtain random coincidence data.

The reconstructing module 1503 may be configured to reconstruct the image with the scanning data by taking the random coincidence data into account.

In an example, the obtaining module 1501 may also be configured to obtain a single-photon counting rate for each of the real crystals, and obtain the crystal receiving efficiency for the real crystal according to the single-photon counting rate for the real crystal.

In an example, when obtaining the single-photon counting rate for each of the real crystals, the obtaining module 1501 may be configured to obtain a number of single-photons received by the real crystal, and obtain the single-photon counting rate for the real crystal according to the number of single-photons and time for receiving the single-photons.

In another example, when obtaining the single-photon counting rate for each of the real crystals, the obtaining module 1501 may be configured to: obtain a plurality of single-photon counting components corresponding to a scanning position; obtain a number of single-photons received by a virtual crystal associated with the scanning position according to the plurality of single-photon counting components; obtain a single-photon counting rate for the virtual crystal according to the number of single-photons received by the virtual crystal and scanning time corresponding to the scanning position; and obtain the single-photon counting rate for each of the real crystal associated with the virtual crystal according to the single-photon counting rate for the virtual crystal.

Where, each of the single-photon counting components is a number of single-photons received by a real crystal associated with the virtual crystal when the scanning position moves to the real crystal, and the scanning position moving to the real crystal indicates that the real crystal locates at an axial position which corresponds to the scanning position. Further, when the scanning position moving to the real crystal, the real crystal and the virtual crystal have the same relative position relationship with the scanning position.

In an example, when obtaining the crystal receiving efficiency for the real crystal according to the single-photon counting rate for the real crystal, the obtaining module 1501 may be configured to, under different doses, obtain the crystal receiving efficiency for the real crystal according to the single-photon counting rate for the real crystal and a function indicating relationship between single-photon counting rate and crystal receiving efficiency for the real crystal, wherein the function is obtained according to the crystal receiving efficiency under different doses; or, the obtaining module 1501 may be configured to, under the same dose, obtain a ratio between the single-photon counting rate for the real crystal and a mean value of the single-photon counting rates for all the real crystals as the crystal receiving efficiency.

In an example, when denoising the delay random coincidence data according to the crystal receiving efficiency for the real crystal to obtain random coincidence data, the processing module 1502 may be configured to: determine two virtual crystals on the response line and each of real crystals associated with the two virtual crystals on the response line, and obtain crystal receiving efficiency for each of the determined real crystals; obtain crystal pair receiving efficiency for the two virtual crystals according to the crystal receiving efficiency for each of the determined real crystals; and denoise the delay random coincidence data according to the crystal pair receiving efficiency to obtain random coincidence data.

In an example, when obtaining crystal pair receiving efficiency for the two virtual crystals according to the crystal receiving efficiency for each of the determined real crystals, the processing module 1502 may be configured to, for the virtual crystal i and the virtual crystal j on the response line, obtain the crystal pair receiving efficiency for the virtual crystal i and the virtual crystal j according to the crystal receiving efficiency form number of real crystals associated with the virtual crystal i on the response line and the crystal receiving efficiency for m number of real crystals associated with the virtual crystal j on the response line.

In an example, when denoising the delay random coincidence data according to the crystal pair receiving efficiency to obtain random coincidence data, the processing module 1502 may be configured to, obtain the random coincidence data for the virtual crystal i and the virtual crystal j by denoising delay random coincidence data for the virtual crystal i and the virtual crystal 1, delay random coincidence data for the virtual crystal j and the virtual crystal k and delay random coincidence data for the virtual crystal l and the virtual crystal k according to a set A of virtual crystals including the virtual crystal i, a set B of virtual crystals including the virtual crystal j, crystal pair receiving efficiency for the virtual crystal i and the virtual crystal l, crystal pair receiving efficiency for the virtual crystal j and the virtual crystal k and crystal pair receiving efficiency for the virtual crystal l and the virtual crystal k, wherein i, j, k and l are non-negative integers; the virtual crystal l belongs to the set B, and the virtual crystal k belongs to the set A.

The examples below may be implemented with software, which may further describe how the device for reconstructing image runs the control logic. In an example, the control logic of the present disclosure may be understood as machine executable instructions stored in the machine readable storage medium 1402. When the processor 1401 of the device for reconstructing image in the present disclosure executes the control logic, the processor 1401 may execute corresponding machine executable instructions of the control logic stored on the machine readable storage medium 1402 to:

obtain scanning data for a subject in a continuous incremental scanning mode;

associate a real crystal with one or more virtual crystal;

obtain delay random coincidence data of a response line according to the scanning data, wherein the response line is a line connecting two virtual crystals for obtaining coincidence data;

obtain random coincidence data by denoising the delay random coincidence data based on crystal receiving efficiency for each of the real crystals; and reconstruct the image with the scanning data by taking the random coincidence data into account.

In an example, the machine executable instructions may also cause the processor 1401 to: obtain a single-photon counting rate for each of the real crystals, and obtain the crystal receiving efficiency for the real crystal according to the single-photon counting rate for the real crystal.

In another example, for obtaining the single-photon counting rate for each of the real crystals, the machine executable instructions cause the processor to: obtain a number of single-photons received by the real crystal; and obtain the single-photon counting rate for the real crystal according to the number of single-photons and time for receiving the single-photons.

In another example, for obtaining the single-photon counting rate for each of the real crystals, the machine executable instructions cause the processor to: obtain a plurality of single-photon counting components corresponding to a scanning position of the subject; obtain a number of single-photons received by a virtual crystal associated with the scanning position according to the plurality of the single-photon counting components; obtain a single-photon counting rate for the virtual crystal according to the number of single-photons received by the virtual crystal and scanning time corresponding to the scanning position; and obtain the single-photon counting rate for each of the real crystals associated with the virtual crystal according to the single-photon counting rate for the virtual crystal, wherein each of the single-photon counting components is a number of single-photons received by a real crystal when the real crystal moves to the scanning position and the real crystal and the virtual crystal have the same relative position relationship with the scanning position.

In an example, when obtaining the crystal receiving efficiency for the real crystal according to the single-photon counting rate for the real crystal, the machine executable instructions cause the processor to: under different doses, obtain the crystal receiving efficiency for the real crystal according to the single-photon counting rate for the real crystal and a function indicating relationship between single-photon counting rate and crystal receiving efficiency for the real crystal, wherein the function is obtained according to the crystal receiving efficiency under different doses.

In another example, when obtaining the crystal receiving efficiency for the real crystal according to the single-photon counting rate for the real crystal, the machine executable instructions cause the processor to: under the same dose, obtain a ratio between the single-photon counting rate for the real crystal and a mean value of the single-photon counting rates for all the real crystals as the crystal receiving efficiency.

In an example, when obtaining the random coincidence data by denoising the delay random coincidence data according to the crystal receiving efficiency for the real crystal, the machine-executable instructions cause the processor to: determine two virtual crystals on the response line and each of real crystals associated with the two virtual crystals on the response line; obtain crystal receiving efficiency for each of the determined real crystals; obtain crystal pair receiving efficiency for the two virtual crystals according to the crystal receiving efficiency for each of the determined real crystals; and obtain the random coincidence data by denoising the delay random coincidence data according to the crystal pair receiving efficiency.

In an example, assuming that the two virtual crystal are for the virtual crystal i and the virtual crystal j on the response line, wherein i, j and m are non-negative integers, when obtaining crystal pair receiving efficiency for the two virtual crystals according to the crystal receiving efficiency for each of the determined real crystals, the machine executable instructions cause the processor to: obtain the crystal pair receiving efficiency for the virtual crystal i and the virtual crystal j according to the crystal receiving efficiency for m number of real crystals associated with the virtual crystal i on the response line and the crystal receiving efficiency for m number of real crystals associated with the virtual crystal j on the response line.

In an example, assuming that the virtual crystal i belongs to a set A comprising m number of virtual crystals, and the virtual crystal j belongs to a set B comprising m number of virtual crystals, wherein i, j, k and l are non-negative integers, when obtaining the random coincidence data by denoising the delay random coincidence data according to the crystal pair receiving efficiency, the machine executable instructions cause the processor to: obtain the random coincidence data for the virtual crystal i and the virtual crystal j by denoising delay random coincidence data for the virtual crystal i and the virtual crystal l among the set B, delay random coincidence data for the virtual crystal j and the virtual crystal k among the set A and delay random coincidence data for the virtual crystal l and the virtual crystal k according to crystal pair receiving efficiency for the virtual crystal i and the virtual crystal 1, crystal pair receiving efficiency for the virtual crystal j and the virtual crystal k and crystal pair receiving efficiency for the virtual crystal l and the virtual crystal k.

For the device examples, since they substantially correspond to the method examples, the correlations therebetween may refer to part of the method examples. The device examples described above are merely illustrative, wherein units described as separate components may be or may not be physically separated, and components displayed as units may be or may not be physical units, i.e., may be located in one place, or may be distributed to a plurality of network elements. Part or all of the modules may be selected according to actual requirements to achieve the purpose of the solution of the present disclosure. Those skilled in the art will understand and implement it without creative work.

The examples set forth above are only illustrated as preferred examples of this disclosure and are not intended to limit this disclosure. All modifications, equivalent substitutions and improvements made within the spirit and principles of this disclosure shall fall within the protection scope of this disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of reconstructing image comprising:
obtaining scanning data for a subject in a continuous incremental scanning mode of a real scanning system including real crystals for detection, the scanning data including information of single-photons received by each of the real crystals when the real crystal relatively moves to a scanning position on the subject in the continuous incremental scanning mode;
constructing a virtual scanning system including a plurality of virtual crystals, each of the virtual crystals being associated with one or more real crystals each having a same relative position relationship with a respective scanning position on the subject in the real scanning system as the virtual crystal with the respective scanning position in the virtual scanning system, a size of each of the virtual crystals being the same as a size of each of the real crystals;
determining, based on the scanning data, delay random coincidence data of two virtual crystals connected by a response line in the virtual scanning system, the response line corresponding to a particular scanning position on the subject;
denoising the delay random coincidence data based on a crystal receiving efficiency for each of a plurality of real crystals associated with the two virtual crystals and the particular scanning position; and
reconstructing an image with the scanning data by using the denoised delay random coincidence data,
wherein denoising the delay random coincidence data comprises:
determining a respective crystal receiving efficiency of each of the plurality of real crystals;
determining a crystal pair receiving efficiency for the two virtual crystals according to the crystal receiving efficiencies of the plurality of real crystals; and
denoising the delay random coincidence data according to the determined crystal pair receiving efficiency,
wherein a first virtual crystal of the two virtual crystals is associated with a plurality of first real crystals,
wherein a second virtual crystal of the two virtual crystals is associated with a plurality of second real crystals, each of the first real crystals corresponds to a respective one of the second real crystals for the particular scanning position, and
wherein determining the crystal pair receiving efficiency for the two virtual crystals comprises:
multiplying a first crystal receiving efficiency for each of the first real crystals with a second crystal receiving efficiency for a second real crystal corresponding to the first real crystal to get a multiplied result; and
determining the crystal pair receiving efficiency for the two virtual crystals by averaging the multiplied results.

2. The method according to claim 1, further comprising:
obtaining a single-photon counting rate for each of the plurality of real crystals; and
generating the crystal receiving efficiency for the real crystal according to the single-photon counting rate for the real crystal.

3. The method according to claim 2, wherein obtaining the single-photon counting rate for the real crystal comprises:
determining a number of single-photons received by the real crystal according to the scanning data; and
generating the single-photon counting rate for the real crystal according to the number of single-photons and a time for receiving the single-photons.

4. The method according to claim 2, wherein obtaining the single-photon counting rate for the real crystal comprises:
determining a plurality of single-photon counting components corresponding to the particular scanning position of the subject, wherein each of the single-photon counting components includes a number of single-photons received by a corresponding real crystal of the plurality of real crystals when the corresponding real crystal moves to the particular scanning position;
determining, according to the plurality of single-photon counting components, a number of single-photons received by one of the two virtual crystals associated with the real crystal;
generating a single-photon counting rate for the one of the two virtual crystals according to the number of single-photons received by the one of the two virtual crystals and scanning time corresponding to the particular scanning position; and
generating the single-photon counting rate for the real crystal according to the single-photon counting rate for the one of the two virtual crystals and a proportional relationship between real crystals associated with the one of the two virtual crystals.

5. The method according to claim 2, wherein generating the crystal receiving efficiency for the real crystal according to the single-photon counting rate for the real crystal comprises:
generating the crystal receiving efficiency for the real crystal according to the single-photon counting rate for the real crystal and a relationship between single-photon counting rate and crystal receiving efficiency for the real crystal under different doses.

6. The method according to claim 5, further comprising:
determining, under a particular dose, a single-photon counting rate for the real crystal and a mean value of single-photon counting rates for a number of real crystals including the real crystal;
determining a crystal receiving efficiency of the real crystal under the particular dose based on the determined single-photon counting rate for the real crystal and the mean value of single-photon counting rates of the number of real crystals; and
determining the relationship based on a ratio between the determined crystal receiving efficiency of the real crystal and the single-photon counting rate under the particular dose.

7. The method according to claim 2, wherein generating the crystal receiving efficiency for the real crystal according to the single-photon counting rate for the real crystal comprises:
under a same dose, determining a ratio between the single-photon counting rate for the real crystal and a mean value of the single-photon counting rates for a number of real crystals including the real crystal; and
taking the determined ratio as the crystal receiving efficiency for the real crystal.

8. The method according to claim 1, further comprising:
obtaining random coincidence data by, with an assumption that the two virtual crystals are virtual crystal i and virtual crystal j on the response line, the virtual crystal i belonging to a set A comprising m number of first virtual crystals and the virtual crystal j belonging to a set B comprising m number of second virtual crystals, denoising:
  delay random coincidence data for the virtual crystal i and a virtual crystal 1 among the set B according to a crystal pair receiving efficiency for the virtual crystal i and the virtual crystal 1,
  delay random coincidence data for the virtual crystal j and a virtual crystal k among the set A according to a crystal pair receiving efficiency for the virtual crystal j and the virtual crystal k, and
  delay random coincidence data for the virtual crystal 1 and the virtual crystal k according to a crystal pair receiving efficiency for the virtual crystal 1 and the virtual crystal k,
  wherein i, j, k and l are non-negative integers; and
reconstructing the image with the scanning data by using the obtained random coincidence data.

9. A device for reconstructing image applied to medical equipment comprising real crystals, the device comprising:
a processor configured to execute machine executable instructions corresponding to control logic for reconstructing image stored on a machine readable storage medium such that when the machine executable instructions are executed, the processor is caused to:
  obtain scanning data for a subject in a continuous incremental scanning mode of the medical equipment;
  associate each of the real crystals with one or more virtual crystals in a virtual scanning system, a size of each of the virtual crystals being the same as a size of each of the real crystals;
  determine, according to the scanning data, delay random coincidence data of two virtual crystals connected by a response line in the virtual scanning system;
  obtain random coincidence data by denoising the delay random coincidence data based on a crystal receiving efficiency for each of a plurality of real crystals associated with the two virtual crystals; and
  reconstruct an image with the scanning data by taking the random coincidence data into account,
wherein the machine executable instructions further cause the processor to:
  obtain a single-photon counting rate for each of the real crystals; and
  determine the crystal receiving efficiency for the real crystal according to the single-photon counting rate for the real crystal, and
wherein the machine executable instructions cause the processor to obtain the single-photon counting rate for each of the real crystals by
  obtaining a plurality of single-photon counting components corresponding to a scanning position of the subject;
  determining a number of single-photons received by a virtual crystal associated with the scanning position according to the plurality of single-photon counting components;
  determining a single-photon counting rate for the virtual crystal according to the number of single-photons received by the virtual crystal and scanning time corresponding to the scanning position; and
  generating the single-photon counting rate for the real crystal associated with the virtual crystal according to the single-photon counting rate for the virtual crystal,
  wherein each of the single-photon counting components is a number of single-photons received by a real crystal when the real crystal moves to the scanning position and the real crystal and the virtual crystal have the same relative position relationship with the scanning position.

10. The device according to claim 9, wherein the machine executable instructions cause the processor to obtain the single-photon counting rate for each of the real crystals by
  determining a number of single-photons received by the real crystal; and
  generating the single-photon counting rate for the real crystal according to the number of single-photons and a time for receiving the single-photons.

11. The device according to claim 9, wherein the machine executable instructions cause the processor to determine the crystal receiving efficiency for the real crystal according to the single-photon counting rate for the real crystal by
  determining the crystal receiving efficiency for the real crystal according to the single-photon counting rate for the real crystal and a function indicating a relationship between single-photon counting rate and crystal receiving efficiency for the real crystal under different doses.

12. The device according to claim 9, wherein the machine executable instructions cause the processor to determine the crystal receiving efficiency for the real crystal according to the single-photon counting rate for the real crystal by
  under a same dose, determining a ratio between the single-photon counting rate for the real crystal and a mean value of the single-photon counting rates for all the real crystals; and
  taking the ratio as the crystal receiving efficiency for the real crystal.

13. The device according to claim 9, wherein the machine executable instructions cause the processor to obtain the random coincidence data by denoising the delay random coincidence data according to the crystal receiving efficiency for the real crystal by
  determining two virtual crystals on the response line and real crystals associated with the two virtual crystals on the response line;
  determining a crystal receiving efficiency for each of the determined real crystals;
  generating a crystal pair receiving efficiency for the two virtual crystals according to the crystal receiving efficiency for each of the determined real crystals; and
  obtaining the random coincidence data by denoising the delay random coincidence data according to the crystal pair receiving efficiency.

14. The device according to claim 13, wherein the machine executable instructions cause the processor to generate the crystal pair receiving efficiency for the two virtual crystals by
  with an assumption that the two virtual crystal are virtual crystal i and virtual crystal j on the response line, determining m number of first real crystals associated with the virtual crystal i on the response line and m number of second real crystals associated with the virtual crystal j on the response line, i, j and m being non-negative integers, and generating the crystal pair receiving efficiency for the virtual crystal i and the virtual crystal j according to crystal receiving efficiencies for the m number of first real crystals and crystal receiving efficiencies for the m number of second real crystals.

15. The device according to claim 13, wherein the machine executable instructions cause the processor to obtain the random coincidence data by denoising the delay random coincidence data according to the crystal pair receiving efficiency by
with an assumption that the two virtual crystals are virtual crystal i and virtual crystal j on the response line, the virtual crystal i belonging to a set A comprising m number of first virtual crystals and the virtual crystal j belonging to a set B comprising m number of second virtual crystals,
obtaining the random coincidence data by denoising:
delay random coincidence data for the virtual crystal i and a virtual crystal 1 among the set B according to a crystal pair receiving efficiency for the virtual crystal i and the virtual crystal 1,
delay random coincidence data for the virtual crystal j and a virtual crystal k among the set A according to a crystal pair receiving efficiency for the virtual crystal j and the virtual crystal k, and
delay random coincidence data for the virtual crystal 1 and the virtual crystal k according to a crystal pair receiving efficiency for the virtual crystal 1 and the virtual crystal k,
wherein i, j, k and l are non-negative integers.

16. A non-transitory computer-readable storage medium having instructions stored thereon which, when executed by one or more processors, cause the one or more processors to perform a method of reconstructing image, the method comprising:
obtaining scanning data for a subject in a continuous incremental scanning mode of a real scanning system including real crystals for detection, the scanning data including information of single-photons received by each of the real crystals when the real crystal relatively moves to a scanning position on the subject in the continuous incremental scanning mode;
constructing a virtual scanning system including a plurality of virtual crystals, each of the virtual crystals being associated with one or more real crystals each having a same relative position relationship with a respective scanning position on the subject in the real scanning system as the virtual crystal with the respective scanning position in the virtual scanning system, a size of each of the virtual crystals being the same as a size of each of the real crystals;
determining, based on the scanning data, delay random coincidence data of two virtual crystals connected by a response line in the virtual scanning system, the response line corresponding to a particular scanning position on the subject;
denoising the delay random coincidence data based on a crystal receiving efficiency for each of a plurality of real crystals associated with the two virtual crystals and the particular scanning position; and
reconstructing an image with the scanning data using the denoised delay random coincidence data,
wherein denoising the delay random coincidence data comprises:
determining a respective crystal receiving efficiency of each of the plurality of real crystals;
determining a crystal pair receiving efficiency for the two virtual crystals according to the crystal receiving efficiencies of the plurality of real crystals; and
denoising the delay random coincidence data according to the determined crystal pair receiving efficiency,
wherein a first virtual crystal of the two virtual crystals is associated with a plurality of first real crystals,
wherein a second virtual crystal of the two virtual crystals is associated with a plurality of second real crystals, each of the first real crystals corresponds to a respective one of the second real crystals for the particular scanning position, and
wherein determining the crystal pair receiving efficiency for the two virtual crystals comprises:
multiplying a first crystal receiving efficiency for each of the first real crystals with a second crystal receiving efficiency for a second real crystal corresponding to the first real crystal to get a multiplied result; and
determining the crystal pair receiving efficiency for the two virtual crystals by averaging the multiplied results.

* * * * *